US011414386B2

(12) United States Patent
Thatipally et al.

(10) Patent No.: US 11,414,386 B2
(45) Date of Patent: Aug. 16, 2022

(54) PROCESS FOR THE PREPARATION OF IVACAFTOR AND ITS INTERMEDIATES

(71) Applicant: Laurus Labs Ltd., Hyderabad (IN)

(72) Inventors: Suresh Thatipally, Hyderabad (IN); Venkata Krishna Reddy, Hyderabad (IN); Venkata Lakshmi Narasimha Rao Dammalapati, Hyderabad (IN); Satyanarayana Chava, Hyderabad (IN)

(73) Assignee: Laurus Labs Limited, Hyderabad (IN)

( * ) Notice: Subject to any disclaimer, the term of this patent is extended or adjusted under 35 U.S.C. 154(b) by 46 days.

(21) Appl. No.: 17/022,930

(22) Filed: Sep. 16, 2020

(65) Prior Publication Data

US 2020/0407323 A1 Dec. 31, 2020

Related U.S. Application Data

(62) Division of application No. 16/520,626, filed on Jul. 24, 2019, now Pat. No. 10,815,202, which is a division of application No. 15/755,436, filed as application No. PCT/IB2016/055274 on Sep. 2, 2016, now Pat. No. 10,501,419.

(30) Foreign Application Priority Data

Sep. 2, 2015 (IN) ............................ 4640/CHE/2015
Sep. 30, 2015 (IN) ............................ 5222/CHE/2015
Oct. 23, 2015 (IN) ............................ 5696/CHE/2015

(51) Int. Cl.
*C07D 215/56* (2006.01)
*C07C 235/80* (2006.01)
*C07C 237/20* (2006.01)
*A61K 31/47* (2006.01)

(52) U.S. Cl.
CPC ............ *C07D 215/56* (2013.01); *A61K 31/47* (2013.01); *C07C 235/80* (2013.01); *C07C 237/20* (2013.01)

(58) Field of Classification Search
CPC ... C07D 215/56; C07C 235/80; C07C 237/20; A61K 31/47
See application file for complete search history.

(56) References Cited

U.S. PATENT DOCUMENTS

| 7,495,103 | B2 | 2/2009 | Hadida-Ruah et al. |
| 8,410,274 | B2 | 4/2013 | Hurter et al. |
| 8,476,442 | B2 | 7/2013 | DeMattei et al. |
| 9,573,902 | B2 | 2/2017 | Thatipally |

FOREIGN PATENT DOCUMENTS

| CN | 103044263 | | 4/2013 |
| CN | 103787968 | | 5/2014 |
| CN | 105130891 | A | 12/2015 |
| WO | WO 2014/118805 | | 8/2014 |
| WO | WO 2014/125506 | | 8/2014 |
| WO | 2014/135096 | * | 9/2014 |
| WO | WO 2014/135096 | | 9/2014 |
| WO | WO 2015/128882 | | 9/2015 |

* cited by examiner

*Primary Examiner* — D Margaret M Seaman
(74) *Attorney, Agent, or Firm* — Blank Rome LLP

(57) ABSTRACT

The present invention provides processes for the preparation of ivacaftor using novel intermediates and a process for its preparation.

41 Claims, No Drawings

PROCESS FOR THE PREPARATION OF IVACAFTOR AND ITS INTERMEDIATES

CROSS-REFERENCE TO RELATED APPLICATIONS

This application is a divisional application of and claims the benefit of the filing date and disclosure of U.S. application Ser. No. 16/520,626, filed Jul. 24, 2019, which is a divisional application of and claims the benefit of the filing date and disclosure of U.S. application Ser. No. 15/755,436, filed 26 Feb. 2018, which is a national phase application of and claims the benefit of International Application PCT/IB2016/055274, filed on 2 Sep. 2016, which is based on and claims the benefit of Indian Provisional Application Nos. 4640/CHE/2015, filed on 02 Sep. 2015, entitled "An improved process for preparation of ivacaftor", 5222/CHE/2015, filed on 30 Sep. 2015, entitled "A process for preparation of ivacaftor", and 5696/CHE/2015 filed on 23 Oct. 2015, entitled "A process for preparation of ivacaftor", the content of each of which are incorporated by reference herein.

FIELD OF THE INVENTION

The present invention generally relates to processes for the preparation of ivacaftor or a pharmaceutically acceptable salt thereof using novel intermediates.

BACKGROUND OF THE INVENTION

The drug compound having the adopted name Ivacaftor, has a chemical name N-(2, 4-di-tert-butyl-5-hydroxyphenyl)-1,4-dihydro-4-oxoquinoline-3-carboxamide, and is represented by following Formula I:

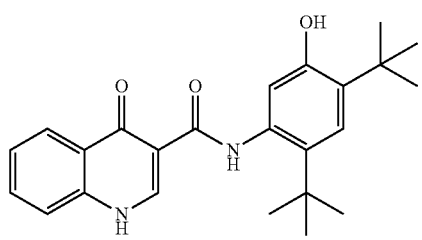

Formula I

Ivacaftor was approved by FDA and marketed by Vertex pharma for the treatment of cystic fibrosis under the brand name KALYDECO® in the form of 150 mg oral tablets and in combination with lumacaftor under the brand name ORKAMBI® in the form of 200 mg/125 mg tablets (Lumacaftor/Ivacaftor) for the treatment of cystic fibrosis.

U.S. Pat. No. 7,495,103 ("the '103 patent") discloses modulators of ATP-binding cassette transporters such as ivacaftor. The '103 patent further discloses a process for the preparation of modulators of ATP-binding cassette transporters such as quinoline compounds; however, ivacaftor process was not specifically disclosed. The '103 patent process includes condensation of 4-oxo-1,4-dihydro-3-quinoline carboxylic acid with aniline in presence of a coupling reagent such as 1-[bis(dimethylamino) methylene]-1H-1,2,3-triazolo[4,5-b]pyridinium 3-oxid hexafluorophosphate (HATU), N,N-diisopropylethylamine (DIEA) in dimethylformamide and then purifying the obtained compound by HPLC. The process disclosed in the '103 patent is schematically represented as follows:

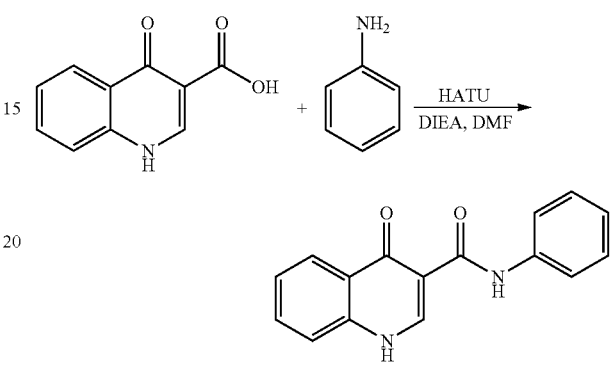

U.S. Pat. No. 8,410,274 ("the '274 patent") specifically discloses a process for preparation of ivacaftor, which involves condensation of 4-oxo-1,4-dihydro-3-quinoline carboxylic acid with 5-amino-2,4-di-(tert-butyl)phenol in presence of a coupling reagent such as HBTU, triethylamine and dimethyl formamide to obtain ivacaftor. The process disclosed in the '274 patent is schematically represented as follows:

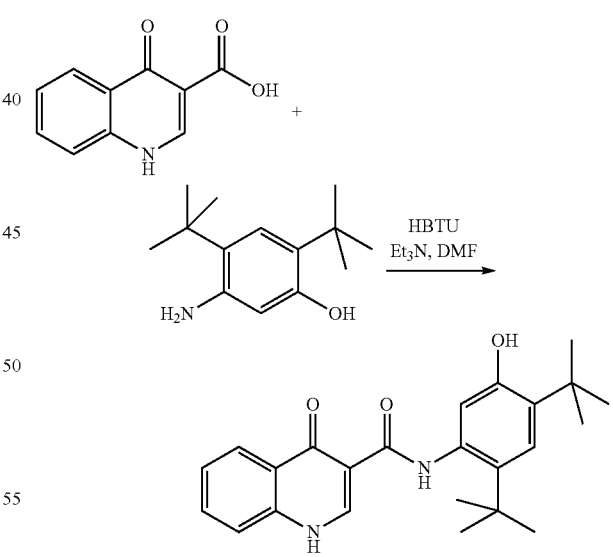

U.S. Pat. No. 8,476,442 ("the '442 patent") discloses a process for preparation of ivacaftor, which involves the coupling of 4-oxo-1,4-dihydro-3-quinoline carboxylic acid with hydroxyl protected amine intermediate in the presence of a coupling reagent such as propane phosphonic anhydride ($T_3P$®) and pyridine followed by deprotection of hydroxyl protection group to obtain ivacaftor. The process disclosed in the '442 patent is schematically represented as follows:

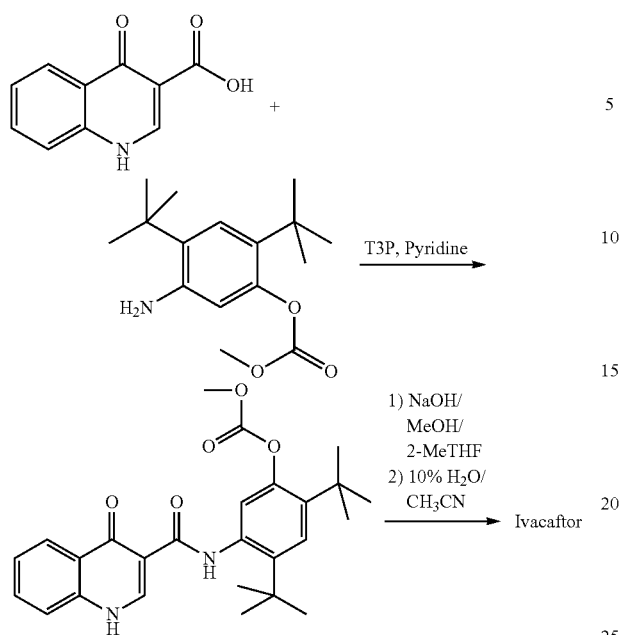

China Patent publication No. 103044263 ("the '263 publication") discloses a process for the preparation of ivacaftor, which involves the coupling of 4-oxo-1,4-dihydro-3-quinoline carboxylic acid chloride with hydroxyl protected amine intermediate in the presence of triethylamine in methylene chloride followed by deprotection of the hydroxyl protection group to obtain ivacaftor. The process disclosed in the '263 publication is schematically represented as follows:

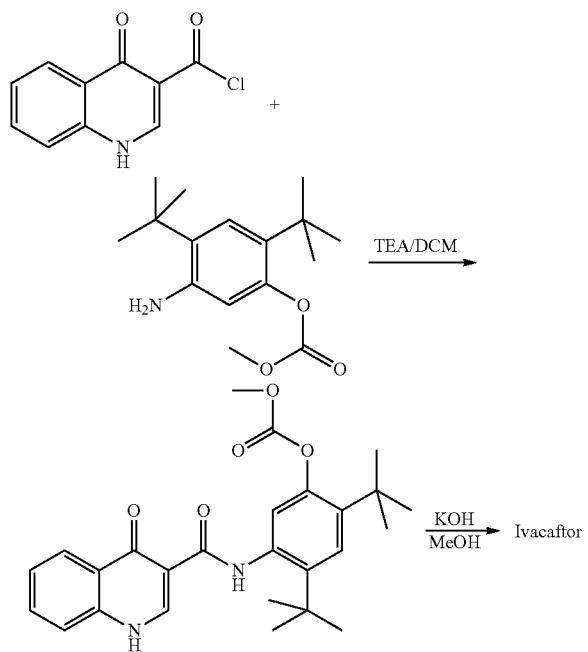

China Patent publication No. 103787968 ("the '968 publication") discloses a process for the preparation of ivacaftor, which involves the coupling of 4-oxo-1,4-dihydro-3-quinoline carboxylic acid ethyl ester with hydroxyl protected amine intermediate in the presence of ethanol followed by deprotection of hydroxyl protection group to obtain ivacaftor. The process disclosed in the '968 publication is schematically represented as follows:

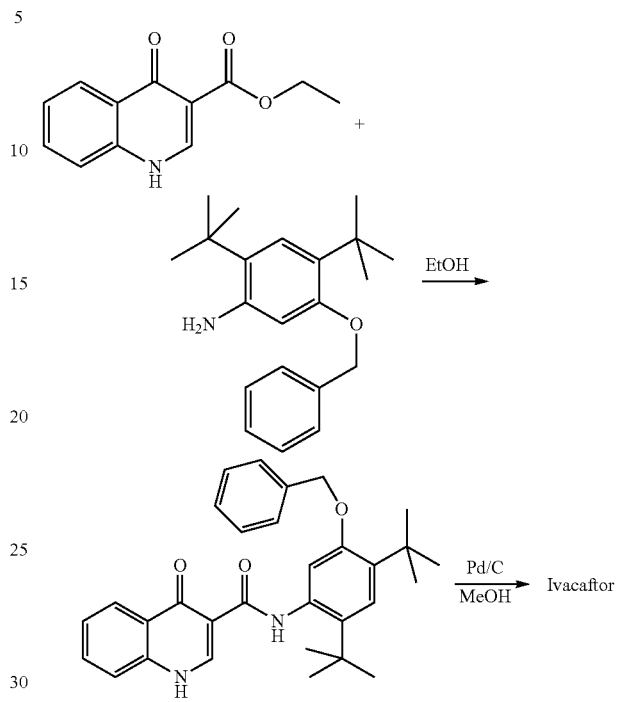

PCT Publication No. WO2014/118805 ("the '805 publication") discloses a process for the preparation of ivacaftor, which involves reaction of malonate intermediate with 5-amino-2,4-di-(tert-butyl)phenol to obtain ester intermediate and finally cyclized to obtain ivacaftor. The process disclosed in the '805 publication is schematically represented as follows:

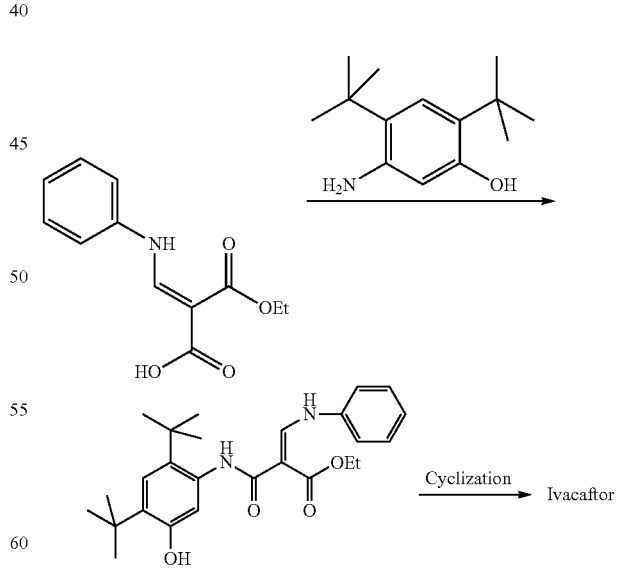

PCT Publication No. WO2014/125506 ("the '506 publication") discloses a process for the preparation of ivacaftor, which involves condensation of 1-benzyl-4-oxo-1,4-dihydroquinoline-3-carboxylic acid with 5-amino-2,4-di-(tert-butyl)phenol in the presence of an amide coupling reagent such as HATU in dimethylformamide and followed by deprotection to obtain ivacaftor. The process disclosed in the '506 publication is schematically represented as follows:
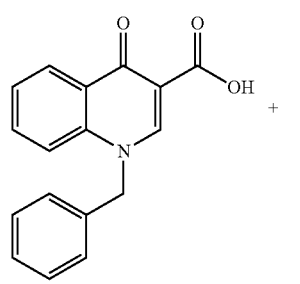
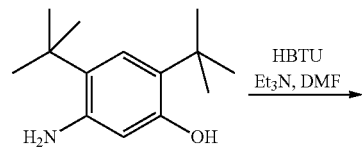
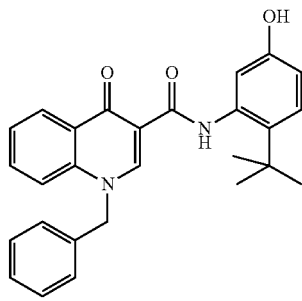
PCT Publication No. WO2014/135096 ("the '096 publication") discloses a process for the preparation of ivacaftor by following methods:
Scheme-1
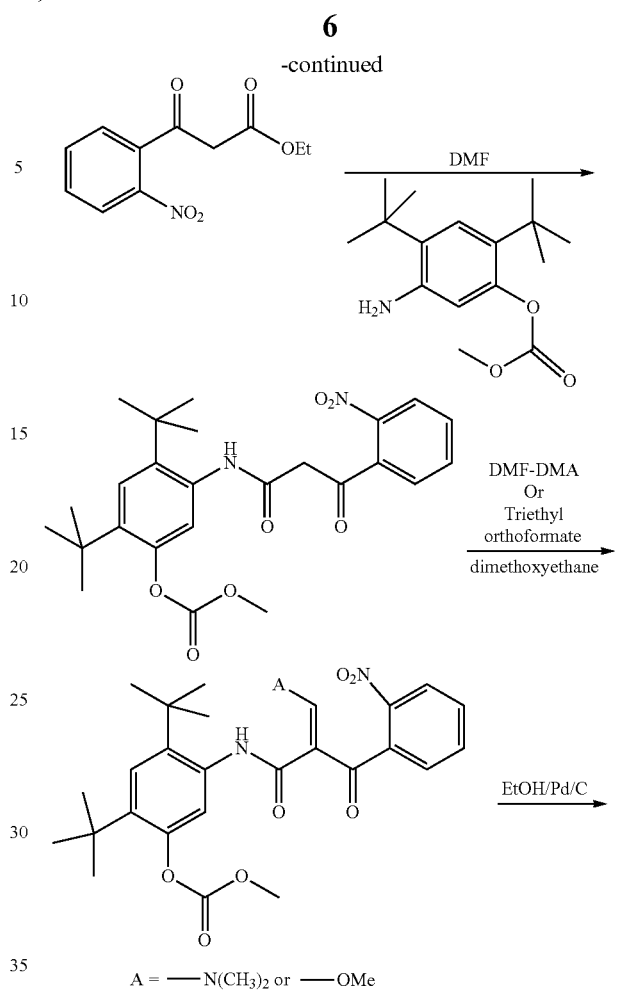
Scheme-2
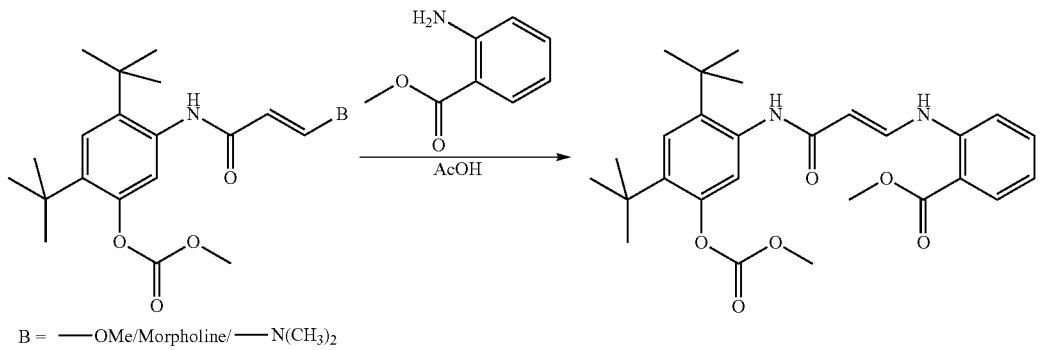

-continued

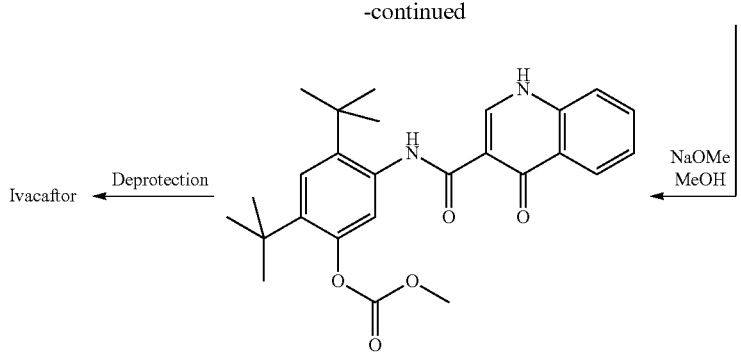

PCT Publication No. WO2015/128882 ("the '882 publication") discloses a process for the preparation of ivacaftor, which involves condensation of 4-oxo-1,4-dihydro-3-quinoline carboxylic acid with 5-amino-2,4-di-(tert-butyl)phenol in presence of a coupling reagent such as EDC HCl and HOBt, triethylamine and dimethyl formamide to obtain ivacaftor. The process disclosed in the '882 patent is schematically represented as follows:

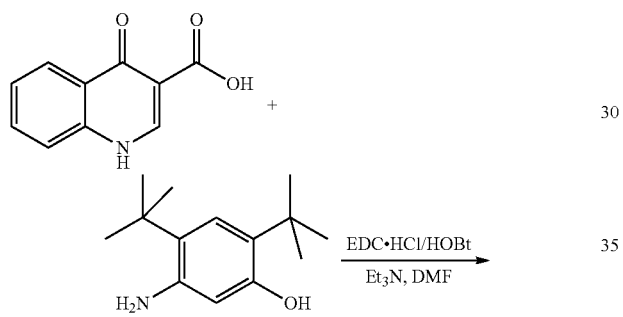

-continued

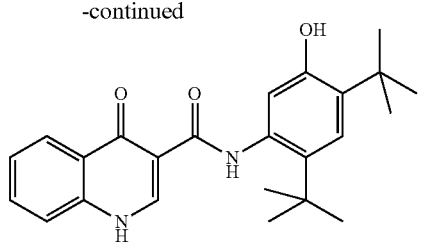

CN Publication No. CN105130891A ("the '891 publication") discloses a process for the preparation of ivacaftor. The process disclosed in the '891 publication is schematically represented as follows:

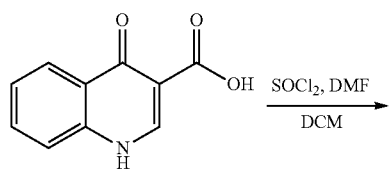

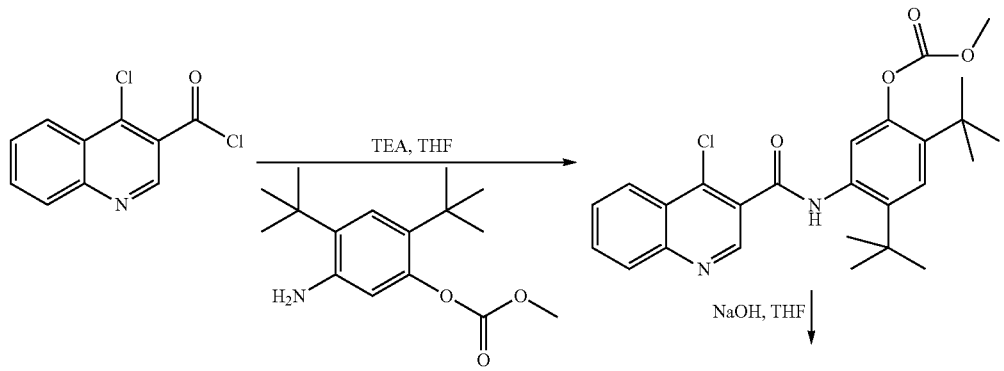

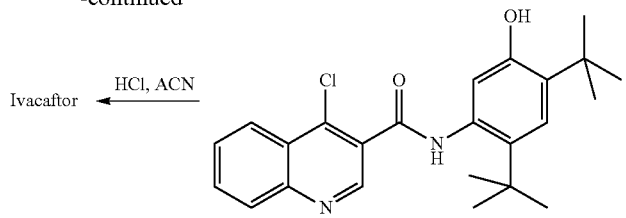

The reported literatures for the preparation of ivacaftor have certain drawbacks, which include use of coupling agents in the amide formation reaction. The use of coupling agents in such a reaction creates unwanted by-products as well as unreacted coupling agents as contaminants, thereby extensive purifications are required in order to eliminate such compounds from the pure product.

There is a need in the art to develop an improved process for the preparation of ivacaftor, which is readily amenable to large scale production. The present inventors focused improved processes for the preparation of ivacaftor with greater yield and higher purity, which process avoids the expensive coupling agents.

SUMMARY OF THE INVENTION

In accordance with one embodiment, the present invention provides a process for the preparation of ivacaftor of Formula I or a pharmaceutically acceptable salt thereof:

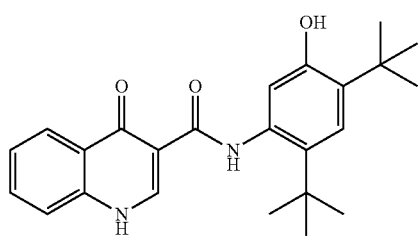

Formula I comprising:
  a) reacting a compound of Formula III with a compound of Formula IV or a salt thereof to obtain a compound of Formula V, and

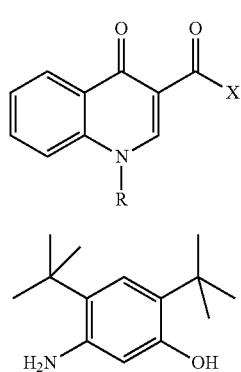

Formula III

Formula IV

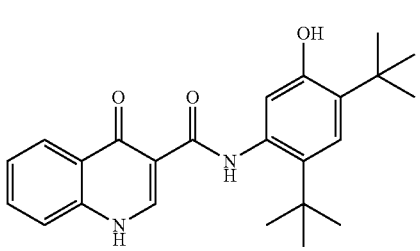

Formula V b) optionally deprotecting the compound of Formula V to obtain ivacaftor of Formula I; wherein 'R' represents hydrogen or a suitable cleavable group, and 'X' represents a suitable leaving group.

In accordance with another embodiment, the present invention provides a process for the preparation of ivacaftor of Formula I or a pharmaceutically acceptable salt thereof, comprising:

a) reacting a compound of Formula III with a compound of Formula IV or a salt thereof to obtain a compound of Formula V, wherein 'R' represents hydrogen or a suitable cleavable group, 'X' represents chloro, bromo or iodo; and b) optionally deprotecting the compound of Formula V to obtain ivacaftor of Formula I.

In accordance with another embodiment, the present invention provides a process for the preparation of ivacaftor of Formula I or a pharmaceutically acceptable salt thereof,

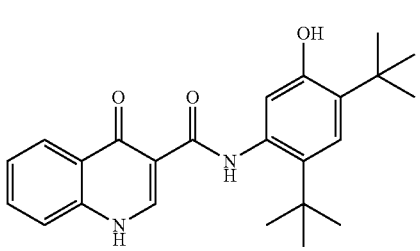

Formula I comprising:
  a) reacting a compound of Formula II with a source of suitable leaving group to obtain a compound of Formula III, Formula II Formula III b) reacting the compound of Formula III with a compound of Formula IV or a salt thereof to obtain a compound of Formula V, and Formula IV Formula V c) optionally deprotecting the compound of Formula V to obtain ivacaftor of Formula I; wherein 'R' represents hydrogen or a suitable cleavable group, and 'X' represents a suitable leaving group.

In accordance with another embodiment, the present invention provides a process for the preparation of ivacaftor of Formula I or a pharmaceutically acceptable salt thereof:

Formula I comprising:

a1) reacting a compound of Formula VI with dimethyl formamide-dimethyl amine complex to obtain a compound of Formula VII, Formula VI Formula VII wherein 'X' represents halo and '$R_1$' represents either hydrogen or a suitable protecting group;

b1) reacting the compound of Formula VII with a source of ammonia to obtain a compound of Formula VIII, and Formula VIII c1) cyclizing the compound of Formula VIII to obtain Ivacaftor, when $R_1$ is hydrogen, or to obtain a compound of Formula IX, when $R_1$ is a protecting group and then deprotecting the Formula IX to obtain ivacaftor.

Formula IX

In accordance with another embodiment, the present invention provides a process for the preparation of ivacaftor of Formula I or a pharmaceutically acceptable salt thereof: comprising:

a2) reacting a compound of Formula VIb with dimethyl formamide-dimethyl amine complex to obtain a compound of Formula VIIb, Formula VIb
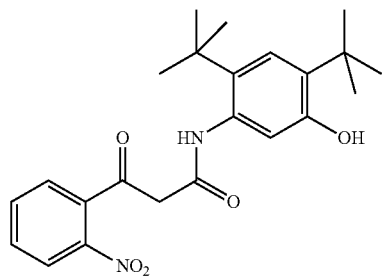

Formula VIIb
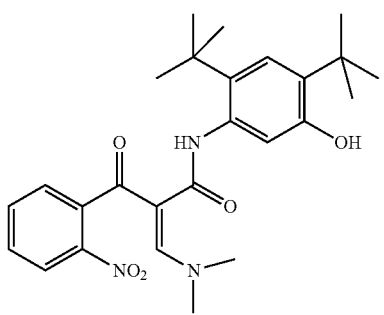

b2) reducing the compound of Formula VIIb in presence of a suitable reducing agent to obtain a compound of Formula X, and Formula X
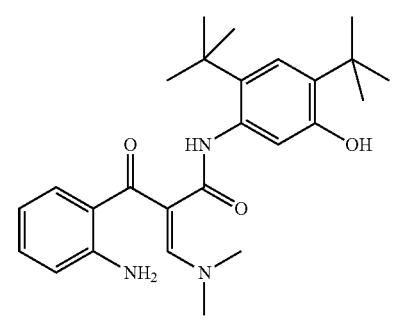

c2) converting the compound of Formula X in to ivacaftor.

In accordance with another embodiment, the present invention provides a process for the preparation of ivacaftor of Formula I or a pharmaceutically acceptable salt thereof; comprising:

a3) reacting a compound of Formula XI with a compound of Formula IVa or a salt thereof to obtain a compound of Formula VI, and Formula XI
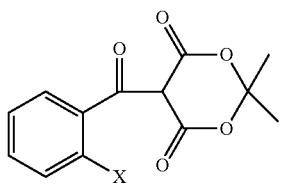

Formula IVa
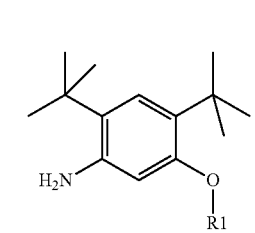

Formula VI
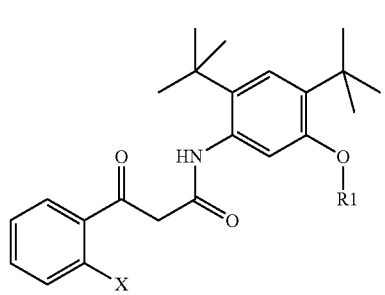

b3) converting the compound of Formula VI in to ivacaftor; wherein when 'X' is halo, then 'R1' is either hydrogen or a suitable protecting group; and when 'X' is nitro, then '$R_1$' is hydrogen.

In accordance with another embodiment, the present invention provides a process for the preparation of ivacaftor of Formula I or a pharmaceutically acceptable salt thereof; comprising:

a4) reacting the compound of Formula XII with a compound of Formula IVa or a salt thereof to obtain a compound of Formula VI, and Formula XII Formula IVa
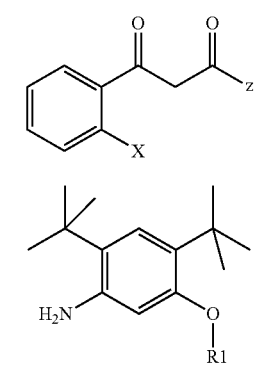

-continued

Formula VI

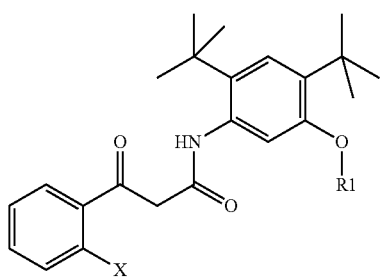

b4) converting the compound of Formula VI in to ivacaftor; wherein when 'X' is halo, then 'R₁' is either hydrogen or a suitable protecting group; when 'X' is nitro, then 'R₁' is hydrogen; and wherein "Z" represents $C_1$-$C_5$ alkoxy or halogen.

In accordance with another embodiment, the present invention provides a compound of Formula VI or a pharmaceutically acceptable salt thereof.

Formula VI

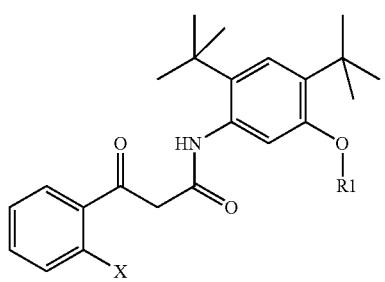

wherein 'X' represents halo and 'R₁' represents either hydrogen or a suitable protecting group.

In accordance with another embodiment, the present invention provides a compound of Formula VIp or a pharmaceutically acceptable salt thereof.

Formula VIp

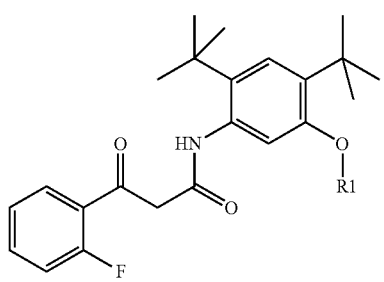

wherein 'R₁' represents either hydrogen or a suitable protecting group.

In accordance with another embodiment, the present invention provides a compound of Formula VIa or a pharmaceutically acceptable salt thereof.

Formula VIa

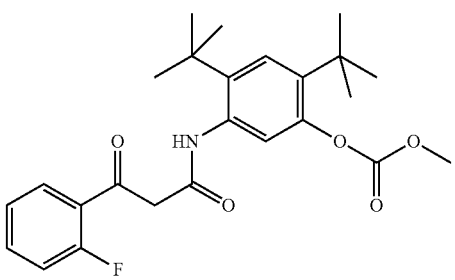

In accordance with another embodiment, the present invention provides a compound of Formula VIp' or a pharmaceutically acceptable salt thereof.

Formula VIp'

In accordance with another embodiment, the present invention provides a compound of Formula VIb or a pharmaceutically acceptable salt thereof.

Formula VIb

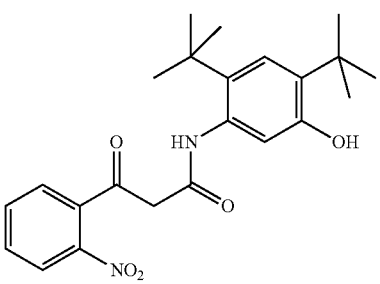

In accordance with another embodiment, the present invention provides a compound of Formula VII or a pharmaceutically acceptable salt thereof.

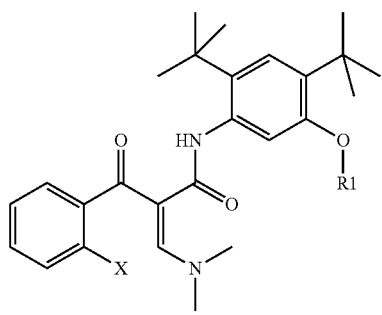

Formula VII wherein 'X' represents halo and 'R₁' represents either hydrogen or a suitable protecting group.

In accordance with another embodiment, the present invention provides a compound of Formula VIIp or a pharmaceutically acceptable salt thereof.

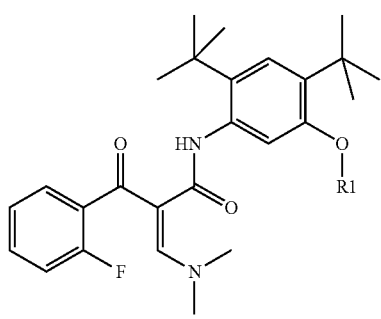

Formula VIIp wherein 'R₁' represents either hydrogen or a suitable protecting group.

In accordance with another embodiment, the present invention provides a compound of Formula VIIa or a pharmaceutically acceptable salt thereof.

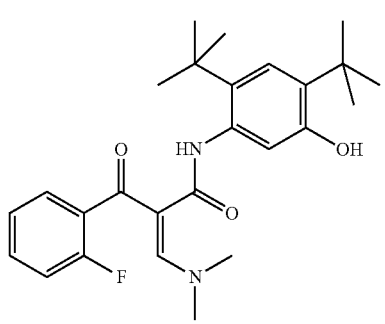

Formula VIIa

In accordance with another embodiment, the present invention provides a compound of Formula VIIp' or a pharmaceutically acceptable salt thereof.

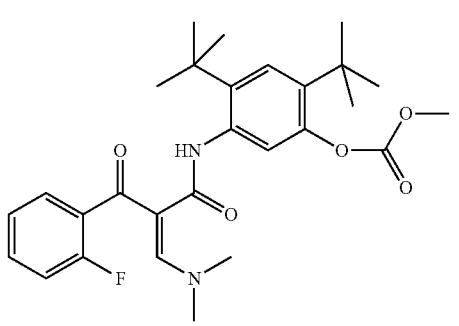

Formula VIIp'

In accordance with another embodiment, the present invention provides a compound of Formula VIIb or a pharmaceutically acceptable salt thereof.

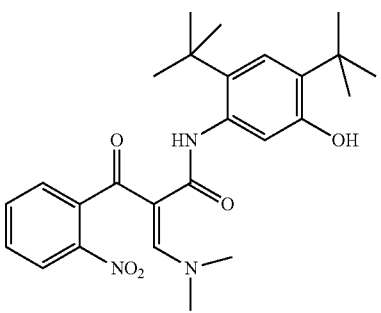

Formula VIIb

In accordance with another embodiment, the present invention provides a compound of Formula VIII or a pharmaceutically acceptable salt thereof.

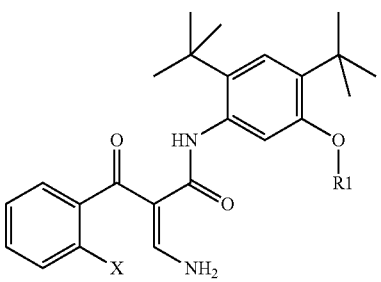

Formula VIII wherein 'X' represents halo and 'R₁' represents either hydrogen or a suitable protecting group.

In accordance with another embodiment, the present invention provides a compound of Formula VIIIp or a pharmaceutically acceptable salt thereof.

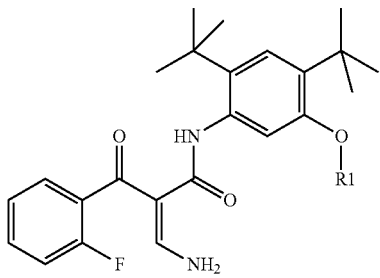

Formula VIIIp wherein 'R₁' represents either hydrogen or a suitable protecting group.

In accordance with another embodiment, the present invention provides a compound of Formula VIIIa or a pharmaceutically acceptable salt thereof.

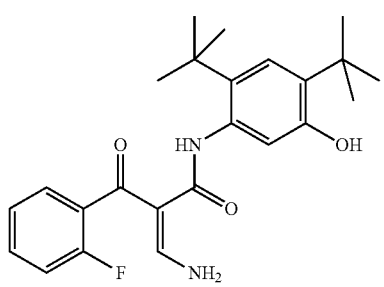

Formula VIIIa

In accordance with another embodiment, the present invention provides a compound of Formula VIIIp' or a pharmaceutically acceptable salt thereof.

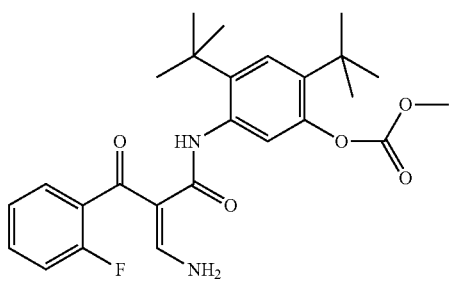

Formula VIIIp'

In accordance with another embodiment, the present invention provides a compound of Formula Xp or a pharmaceutically acceptable salt thereof.

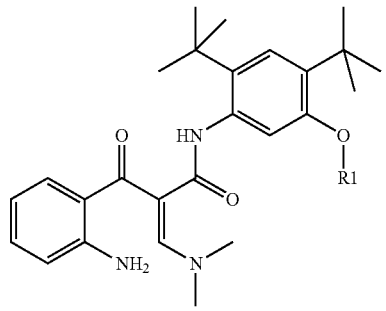

Formula Xp wherein 'R₁' represents either hydrogen or a suitable protecting group.

In accordance with another embodiment, the present invention provides a compound of Formula X or a pharmaceutically acceptable salt thereof.

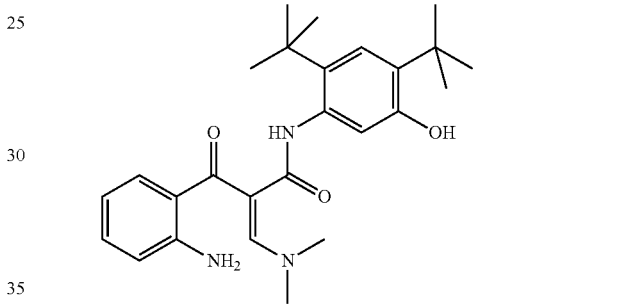

Formula X

In accordance with another embodiment, the present invention provides a compound of Formula Xp' or a pharmaceutically acceptable salt thereof.

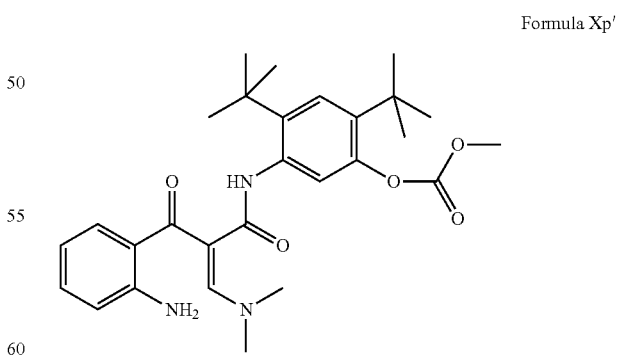

Formula Xp'

In accordance with another embodiment, the present invention provides a process for the preparation of ivacaftor of Formula I or a pharmaceutically acceptable salt thereof, Formula I

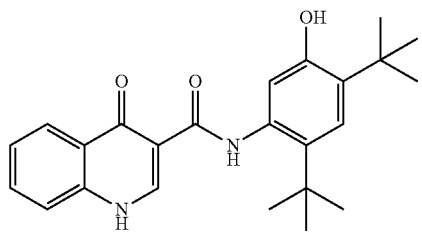

comprising:
a5) reacting a compound of Formula VI with (C$_{1-5}$ alkyl)$_3$-orthoformate to obtain a compound of Formula XIII, Formula VI

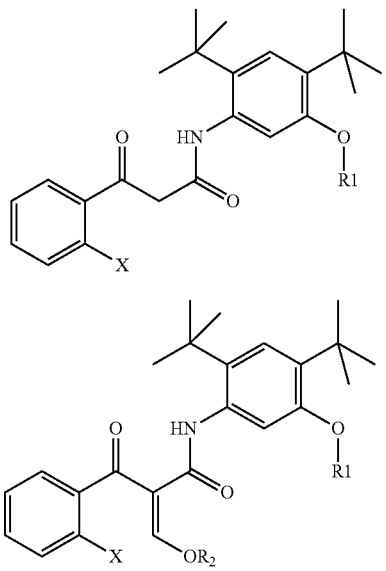

Formula XIII wherein 'X' represents halo and 'R$_1$' represents either hydrogen or a suitable protecting group and wherein 'R$_2$' represents C$_{1-5}$ alkyl;
b5) reacting the compound of Formula XIII with a source of ammonia to obtain a compound of Formula VIII, and Formula VIII

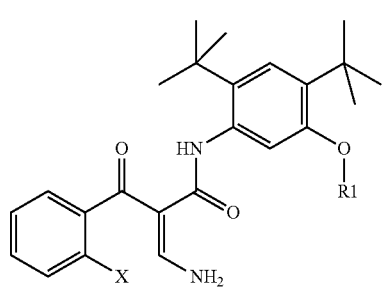

c5) cyclizing the compound of Formula VIII to obtain ivacaftor, when R$_1$ is hydrogen, or to obtain a compound of Formula IX, when R$_1$ is a protecting group and deprotecting the Formula IX to obtain Ivacaftor.

Formula IX

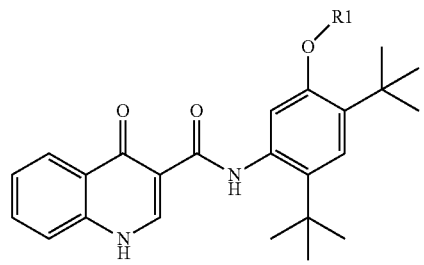

In accordance with another embodiment, the present invention provides a process for the preparation of ivacaftor of Formula I or a pharmaceutically acceptable salt thereof, comprising:
a6) reacting a compound of Formula VIb with (C$_{1-5}$ alkyl)$_3$-orthoformate to obtain a compound of Formula XIV, wherein 'R$_2$' represents C$_{1-5}$ alkyl, Formula VIb

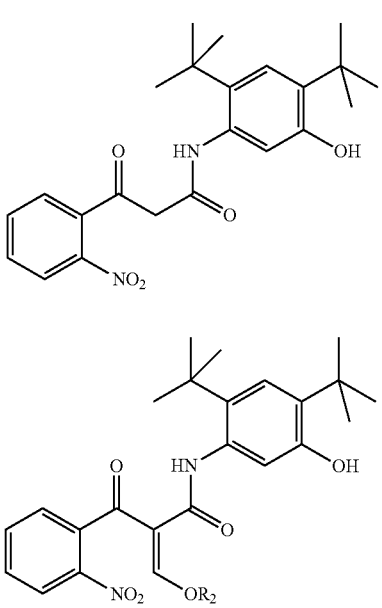

Formula XIV b6) reducing the compound of Formula XIV in presence of a suitable reducing agent to obtain a compound of Formula XV, and Formula XV

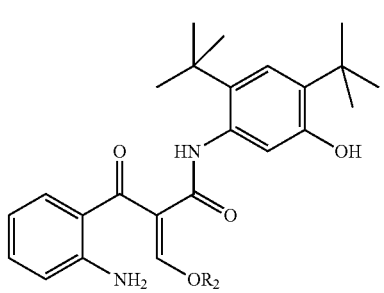

c6) cyclizing the compound of Formula XV in to ivacaftor.

Formula I

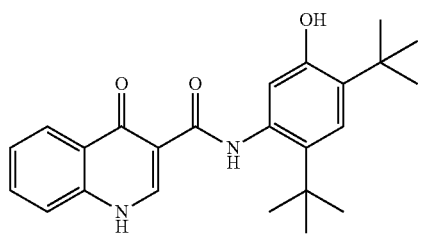

In accordance with another embodiment, the present invention provides a process for the preparation of ivacaftor of Formula I or a pharmaceutically acceptable salt thereof; comprising:

a7) reacting a compound of Formula XVI with a compound of Formula IVa or a salt thereof to obtain a compound of Formula XVII, Formula XVI

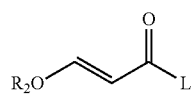

Formula IVa

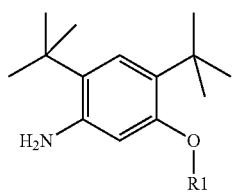

Formula XVII

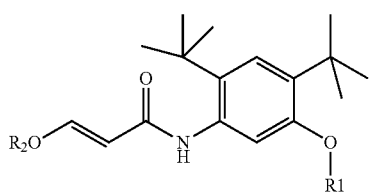

b7) reacting the compound of Formula XVII with a compound of Formula XVIII to obtain a compound of Formula XIII, and Formula XVIII

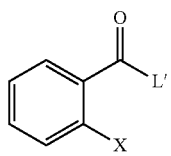

Formula XIII

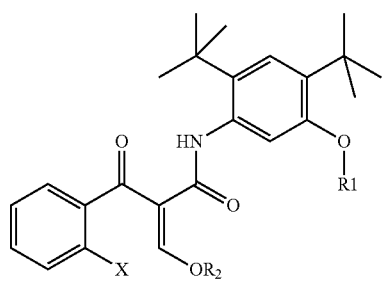

c7) converting the compound of Formula XIII in to ivacaftor; wherein 'X' represents halo or nitro; '$R_1$' represents either hydrogen or a suitable protecting group; '$R_2$' represents $C_{1-5}$ alkyl; L and L' represents a suitable leaving group.

In accordance with another embodiment, the present invention provides a compound of Formula XIII or a pharmaceutically acceptable salt thereof.

Formula XIII

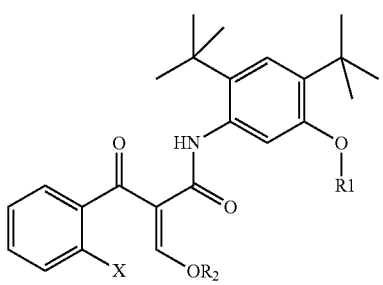

wherein 'X' represents Halo, —$NO_2$ or —$NH_2$, '$R_1$' represents either hydrogen or a suitable protecting group; and '$R_2$' represents $C_{1-5}$ alkyl; provided that wherein when "X" is —$NO_2$ or —$NH_2$ then '$R_1$' is hydrogen.

In accordance with another embodiment, the present invention provides a compound of Formula XIIIa or a pharmaceutically acceptable salt thereof.

Formula XIIIa

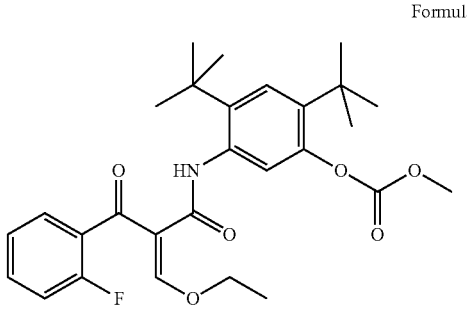

In accordance with another embodiment, the present invention provides a compound of Formula XIIIb or a pharmaceutically acceptable salt thereof.

Formula XIIIb

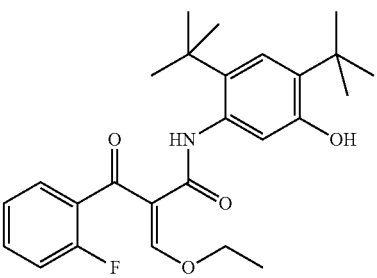

In accordance with another embodiment, the present invention provides a compound of Formula XIIIc, wherein '$R_2$' represents $C_{1-5}$ alkyl, or a pharmaceutically acceptable salt thereof.

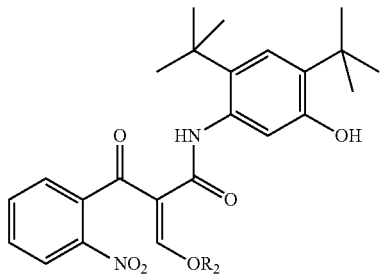

Formula XIIIc

In accordance with another embodiment, the present invention provides a compound of Formula XV, wherein 'R$_2$' represents C$_{1-5}$ alkyl, or a pharmaceutically acceptable salt thereof.

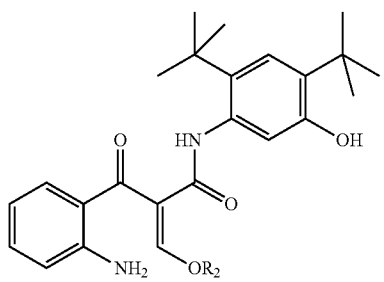

Formula XV

In accordance with another embodiment, the present invention provides a pharmaceutical composition comprising ivacaftor or a pharmaceutically acceptable salt thereof prepared by the processes of the present invention and at least one pharmaceutically acceptable excipient.

DETAILED DESCRIPTION OF THE INVENTION

The present invention provides a process for the preparation of ivacaftor or a pharmaceutically acceptable salt thereof using novel intermediates.

In accordance with one embodiment, the present invention provides a process for the preparation of ivacaftor of Formula I or a pharmaceutically acceptable salt thereof:

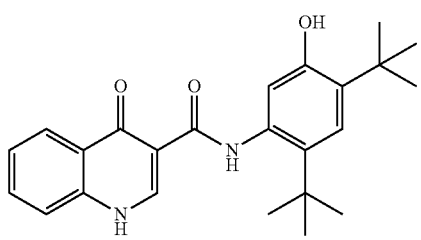

Formula I comprising:
a) reacting a compound of Formula III with a compound of Formula IV or a salt thereof to obtain a compound of Formula V, and

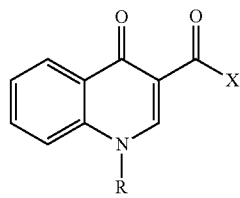

Formula III

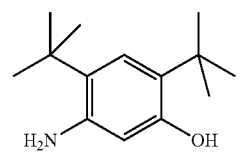

Formula IV

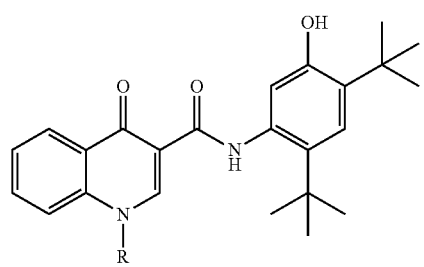

Formula V b) optionally deprotecting the compound of Formula V to obtain ivacaftor of Formula I; wherein 'R' represents hydrogen or a suitable cleavable group and 'X' represents a suitable leaving group.

In accordance with another embodiment, the present invention provides a process for the preparation of ivacaftor of Formula I or a pharmaceutically acceptable salt thereof,

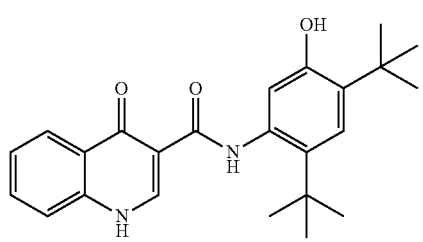

Formula I comprising:
a) reacting a compound of Formula II with a source of suitable leaving group to obtain a compound of Formula III,

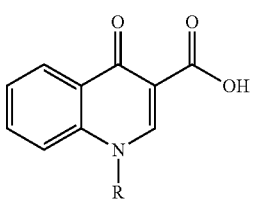

Formula II

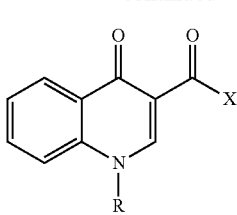

Formula III b) reacting the compound of Formula III with a compound of Formula IV or a salt thereof to obtain a compound of Formula V, and

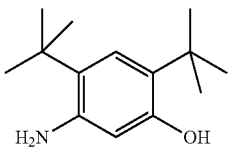

Formula IV

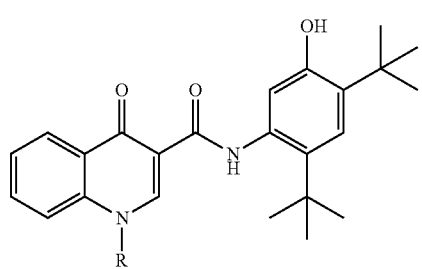

Formula V c) optionally deprotecting the compound of Formula V to obtain ivacaftor of Formula I; wherein 'R' represents hydrogen or a suitable cleavable group and 'X' represents a suitable leaving group.

Unless otherwise specified, the term "suitable cleavable group" used herein the specification includes but is not limited to carbamates such as tertiary butyloxy carbonyl (Boc), carboxy benzoyl (Cbz), fluorenylmethyloxycarbonyl (Fmoc), allyloxycarbonyl (alloc), methyl and ethyl carbamates; cyclic imide derivatives such as phthalimide; amides such as formyl; acetyl, pivaloyl, trityl; substituted or unsubstituted aryls such as benzyl, benzoyl, p-nitrobenzoyl (PNB), p-phenyl benzyl (PPB), 4-methoxy benzyl, 4-trifluoromethyl benzyl, 4-chloro benzyl; and trialkyl silyl groups such as trimethylsilyl (TMS), tert-butyldiphenylsilyl (TBDPS), tert-butyldimethylsilyl (TBS/TBDMS), triisopropylsilyl (TIPS) and the like.

Unless otherwise specified, the term "suitable leaving group" used herein the specification includes but is not limited to chloro, bromo, iodo and the like; mesyl, tosyl, triflate, nosyl and the like.

Unless otherwise specified, the term "source of suitable leaving group" used herein the specification includes but is not limited to thionyl chloride, thionyl bromide, phosphorous oxy chloride, phosphorous pentachloride, phosphorous tribromide, oxalyl chloride, phosphorus triiodide and the like; halides of mesyl, tosyl, nosyl such as chloro, bromo, iodo and the like; triflic acid.

Compound of Formula II and compound of Formula IV or a salt thereof are known in the art and can be prepared by any method known in the art, for example compound of Formula II may be prepared by using the process disclosed in WO2014/125506, and compound of Formula IV or a salt thereof may be prepared by using the process disclosed in applicant's PCT application No. 2016/075703.

The step a) of the aforementioned process involves reaction of compound of Formula II; wherein 'R' represents hydrogen or a suitable cleavable group, with a source of suitable leaving group, may be carried out in a suitable solvent and in presence of a suitable base to obtain a compound of Formula III; wherein 'X' represents a suitable leaving group as mentioned above; preferably chloro or bromo; more preferably chloro.

In a preferred embodiment, the compound of Formula II is used as both protected or unprotected groups at nitrogen and in case of formula II has protecting group at nitrogen atom an optional step of deprotection step is necessary to obtain ivacaftor of Formula I. The suitable cleavable group used herein preferably benzyl group.

The suitable solvent for the reaction of compound of Formula II; wherein 'R' defined as above with a source of suitable leaving group, includes but is not limited to ethers, halogenated solvents, aromatic hydrocarbons, amides, sulfoxides, nitriles and mixtures thereof. Preferably ethers include, but are not limited to tetrahydrofuran, 2-methyl tetrahydrofuran, dimethyl ether, diisopropyl ether, methyl tertiary butyl ether, 1,4-dioxane and the like; halogenated solvents include, but are not limited to methylene chloride, ethylene chloride, chloroform and the like; aromatic hydrocarbons include, but are not limited to toluene, xylene and the like; amides include, but are not limited to dimethyl formamide, dimethyl acetamide, N-methyl pyrrolidinone and the like; sulfoxides include, but are not limited to dimethylsulfoxide, sulfolane and the like; nitriles include, but are not limited to acetonitrile, propionitrile and like and mixtures thereof; preferably methylene chloride, tetrahydrofuran or dimethyl formamide.

Exemplary bases used herein for the reaction of compound of Formula II; wherein 'R' defined as above with a source of suitable leaving group, includes but are not limited to sodium hydroxide, potassium hydroxide, sodium methoxide, sodium ethoxide, sodium-tert-butoxide, potassium-tert-butoxide, sodium carbonate, potassium carbonate, cesium carbonate, sodium bicarbonate, potassium bicarbonate, triethylamine, isopropyl ethylamine, diisopropyl amine, diisopropyl ethylamine, N-methyl morpholine, piperidine, pyridine and the like and mixtures thereof; preferably triethylamine, sodium hydroxide or diisopropyl ethylamine.

The reaction of compound of Formula II; wherein 'R' defined as above with a source of suitable leaving group is carried out at a temperature of about 0° C. to reflux temperature; preferably at 35° C. to about 40° C.

The step b) of the aforementioned process involves reaction of the compound of Formula III; wherein 'R' and 'X' are defined as above, with a compound of Formula IV or a salt thereof, may be carried out in a suitable solvent and in presence of a suitable base to obtain a compound of Formula V; wherein 'R' defined as above.

The suitable solvent for the reaction of compound of Formula III; wherein 'R' and 'X' are defined as above, with a compound of Formula IV or a salt thereof may be carried out in a suitable solvent. The suitable solvent includes but is not limited to ethers, halogenated solvents, aromatic hydrocarbons, amides, sulfoxides, nitriles and mixtures thereof. Preferably ethers include, but are not limited to tetrahydrofuran, 2-methyl tetrahydrofuran, dimethyl ether, diisopropyl ether, methyl tertiary butyl ether, 1,4-dioxane and the like; halogenated solvents include, but are not limited to methylene chloride, ethylene chloride, chloroform and the like; aromatic hydrocarbons include, but are not limited to toluene, xylene and the like; amides include, but are not limited to dimethylformamide, dimethyl acetamide, N-methyl pyrrolidinone and the like; sulfoxides include, but are not limited to dimethylsulfoxide, sulfolane and the like; nitriles include, but are not limited to acetonitrile, propionitrile and like and mixture thereof; preferably methylene chloride, tetrahydrofuran or dimethylformamide.

Exemplary bases used herein for the reaction of compound of Formula III; wherein 'R' and 'X' are defined as above, with a compound of Formula IV or a salt thereof, includes but are not limited to sodium hydroxide, potassium hydroxide, sodium methoxide, sodium ethoxide, sodium-tert-butoxide, potassium-tert-butoxide, sodium carbonate, potassium carbonate, cesium carbonate, sodium bicarbonate, potassium bicarbonate, triethylamine, isopropylethylamine, diisopropyl amine, diisopropyl ethylamine, N-methyl morpholine, piperidine, pyridine and the like and mixture thereof; preferably triethylamine, diisopropyl ethylamine or potassium hydroxide.

The reaction of compound of Formula III; wherein 'R' and 'X' are defined as above, with a compound of Formula IV or a salt thereof is carried out at a temperature of about 0° C. to reflux temperature; preferably at 25° C. to about 40° C.

The step c) of the aforementioned process involves optional step of deprotection of the compound of Formula V; when R is a protecting group which is mentioned as above to obtain ivacaftor of Formula I or a pharmaceutically acceptable salt thereof. The deprotection is carried out in presence of a suitable deprotecting agent and a suitable solvent.

The suitable deprotecting agent used herein for the deprotection of the compound of Formula V; wherein 'R' defined as above includes but is not limited to palladium on carbon, palladium hydroxide, raney nickel, platinum oxide, cericammoniumnitrate (CAN) in presence of hydrogen source such as ammonium formate or hydrogen gas, 2,3-dichloro-5,6-dicyano-1,4-benzoquinone, tetrabutylammonium fluoride, borantribromide, aluminium chloride, acid source such as HCl, HBr, acetic acid, trifluoroacetic acid and the like.

The suitable solvent for deprotection of the compound of Formula V; wherein 'R' defined as above includes but is not limited to alcohols, ketones, nitriles, ethers, amides and mixtures thereof. The alcohols include, but are not limited to methanol, ethanol, isopropanol and the like; ketones include, but are not limited to acetone, methyl isobutyl ketone, methyl ethyl ketone and the like; nitriles include, but are not limited to acetonitrile, propionitrile and the like; ethers include, but are not limited to tetrahydrofuran, 2-methyl tetrahydrofuran, dimethyl ether, diisopropyl ether, methyl tertiary butyl ether, 1,4-dioxane and the like; amides include, but are not limited to dimethyl formamide, dimethyl acetamide, N-methyl pyrrolidinone and the like and mixture thereof; preferably dimethyl formamide.

The deprotection reaction may be carried out at a temperature of about 0° C. to reflux temperature; preferably at 60° C. to about 90° C.

In another embodiment, the present invention provides a process for the preparation of ivacaftor of Formula I or a pharmaceutically acceptable salt thereof:

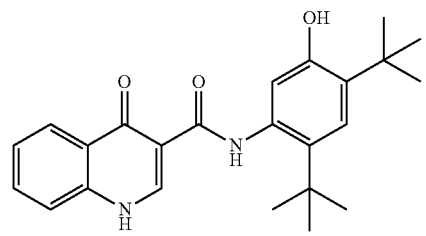

Formula I comprising:

a1) reacting a compound of Formula VI with dimethyl formamide-dimethyl amine complex to obtain a compound of Formula VII,

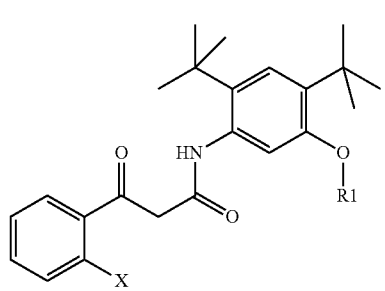

Formula VI

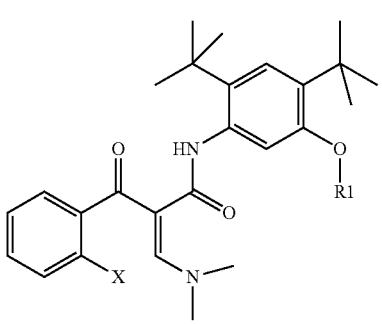

Formula VII wherein 'X' represents halo and '$R_1$' represents either hydrogen or a suitable protecting group;

b1) reacting the compound of Formula VII with a source of ammonia to obtain a compound of Formula VIII, and

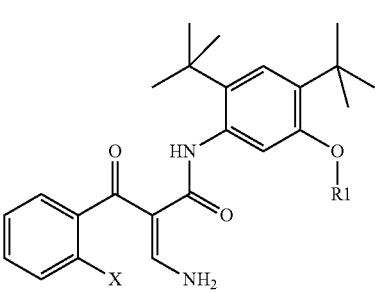

Formula VIII c1) cyclizing the compound of Formula VIII to obtain ivacaftor, when $R_1$ is hydrogen, or to obtain a compound of Formula IX, when $R_1$ is a protecting group and deprotecting the Formula IX to obtain ivacaftor.

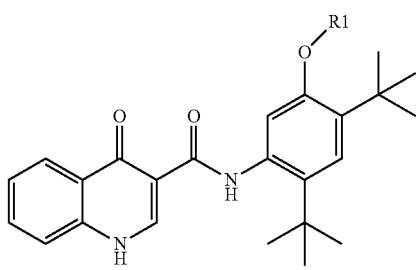

Formula IX

In another embodiment, the starting compound of Formula VI can be prepared according to process described in one or more below mentioned embodiments.

The step a1) of the aforementioned process involves reaction of compound of Formula VI, obtained by the processes described as above with dimethyl formamide-dimethyl amine complex in a suitable organic solvent; wherein 'X' represents halo and '$R_1$' represents either hydrogen or a suitable protecting group.

In a preferred embodiment the exemplary compound of Formula VII can be represented as follows:

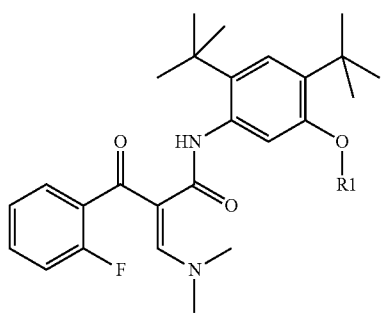

Formula VIIp wherein '$R_1$' represents either hydrogen or a suitable protecting group.

In a further preferred embodiment the exemplary compound of Formula VII can be represented as follows:

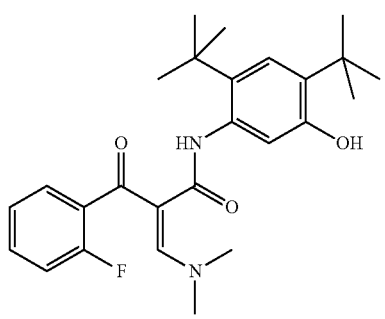

Formula VIIa

The suitable organic solvent used herein for reaction of compound of Formula VI with dimethyl formamide-dimethyl amine complex includes but is not limited to nitriles, ethers, aromatic hydrocarbons and mixtures thereof. The nitriles include, but are not limited to acetonitrile, propionitrile and the like; ethers include, but are not limited to tetrahydrofuran, dimethyl ether, methyl tertiary butyl ether, dimethoxyethane and the like; aromatic hydrocarbons include, but are not limited to toluene, xylene and the like and mixtures thereof; preferably toluene.

The reaction of compound of Formula VI with dimethyl formamide-dimethyl amine complex advantageously carried out at a temperature of about room temperature to reflux temperature; preferably 50° C. to about 75° C.

The step b1) of the aforementioned process involves reaction of the compound of Formula VII with a source of ammonia to obtain a compound of Formula VIII, wherein 'X' and '$R_1$' are defined as above.

In a preferred embodiment the exemplary compound of Formula VIII can be represented as follows:

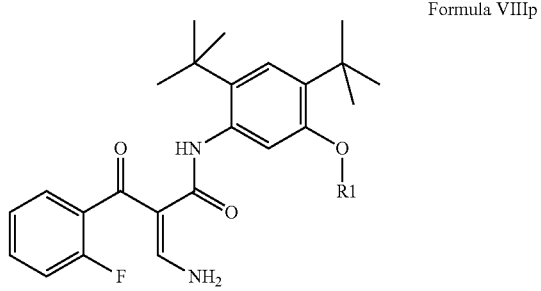

Formula VIIIp wherein '$R_1$' represents either hydrogen or a suitable protecting group.

In a further preferred embodiment the exemplary compound of Formula VIII can be represented as follows:

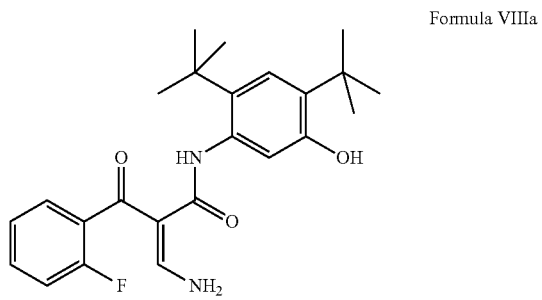 [SMILES: CC(C)(C)c1cc(C(C)(C)C)c(NC(=O)/C(=C\N)C(=O)c2ccccc2F)cc1O]

Formula VIIIa

Exemplary sources of ammonia used herein for the reaction of compound of Formula VII includes but is not limited to ammonia gas, ammonium hydroxide, ammonium acetate, ammonium formate and the like; preferably ammonium hydroxide.

The reaction of the compound of Formula VII with a source of ammonia may be carried out in a suitable solvent. The suitable solvent includes but is not limited to alcohols, amides, aromatic hydrocarbons, water and mixtures thereof. The alcohols include, but are not limited to methanol, ethanol, isopropanol and the like; amides include, but are not limited to dimethyl formamide, dimethyl acetamide, N-methyl pyrrolidinone and the like; aromatic hydrocarbons include, but are not limited to toluene, xylene and the like; water and mixtures thereof; preferably ethanol.

The reaction of the compound of Formula VII with a source of ammonia advantageously carried out at a temperature of about room temperature to reflux temperature; preferably at 20° C. to about 40° C.

The step c1) of the aforementioned process involves cyclization of the compound of Formula VIII to obtain ivacaftor, when $R_1$ is hydrogen, or to obtain a compound of Formula IX, when $R_1$ is a protecting group and deprotecting the Formula IX to obtain ivacaftor.

The cyclization of compound of Formula VIII is carried out in presence of a suitable base to obtain a compound of Formula IX. The suitable base includes but is not limited to inorganic bases such as sodium hydroxide, potassium hydroxide, sodium methoxide, sodium ethoxide, sodium tert-butoxide, potassium tert-butoxide, sodium carbonate, potassium carbonate, cesium carbonate, sodium bicarbonate, potassium bicarbonate, organic bases such as triethylamine, isopropylethylamine, diisopropylamine, diisopropylethylamine, N-methylmorpholine, piperidine, pyridine and the like and mixtures thereof; preferably potassium hydroxide.

The cyclization of compound of Formula VIII is carried out in a suitable solvent. The suitable solvent includes but is not limited to ethers, alcohols, aromatic hydrocarbons, amides, sulfoxides, nitriles and mixtures thereof. Preferably ethers include, but are not limited to tetrahydrofuran, 2-methyl tetrahydrofuran, dimethyl ether, methyl tertiary butyl ether and the like; alcohols include, but are not limited to methanol, ethanol, isopropanol and the like; aromatic hydrocarbons include, but are not limited to toluene, xylene and the like; amides include, but are not limited to dimethylformamide, dimethyl acetamide, N-methyl pyrrolidinone and the like; sulfoxides include, but are not limited to dimethylsulfoxide, sulfolane and the like; nitriles include, but are not limited to acetonitrile, propionitrile and like and mixtures thereof; preferably dimethylformamide.

The deprotection of the compound of Formula IX is carried out in presence of a suitable deprotecting agent and a suitable solvent.

The suitable deprotecting agent used herein for the deprotection of the compound of Formula IX; wherein '$R_1$' defined as above includes but is not limited to acid deprotecting agent such as hydrochloric acid, hydrobromic acid, trifluoro acetic acid and the like and mixture thereof; base deprotecting agent such as potassium carbonate, sodium hydroxide, sodium ethoxide and the like and mixture thereof; preferably potassium carbonate.

The suitable solvent for deprotection of the compound of Formula IX; wherein '$R_1$' defined as above includes but is not limited to alcohols, ketones, ethers, amides, sulfoxides and mixtures thereof. The alcohols include, but are not limited to methanol, ethanol, isopropanol and the like; ketones include, but are not limited to acetone, methyl isobutyl ketone, methyl ethyl ketone and the like; ethers include, but are not limited to tetrahydrofuran, 2-methyl tetrahydrofuran, methyl tertiary butyl ether and the like; amides include, but are not limited to dimethyl formamide, dimethyl acetamide, N-methyl pyrrolidinone and the like; sulfoxides include, but are not limited to dimethylsulfoxide, sulfolane and the like and mixture thereof; preferably dimethyl formamide.

The deprotection reaction may be carried out at a temperature of about 0° C. to reflux temperature; preferably at 90° C. to about 110° C.

In another embodiment, the present invention provides a process for the preparation of compound of Formula VI, comprising: reacting a compound of Formula XI with a compound of Formula IVa or a salt thereof to obtain a compound of Formula VI;

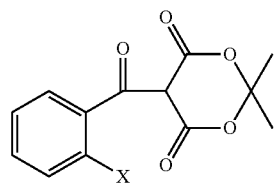

Formula XI

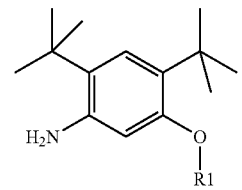

Formula IVa

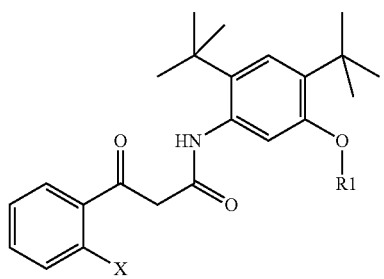

Formula VI wherein when 'X' is halo, then '$R_1$' is either hydrogen or a suitable protecting group; and when 'X' is nitro, then '$R_1$' is hydrogen.

Unless otherwise specified the term suitable hydroxy protecting group used herein are selected from methoxycarbonyl, methoxymethyl (MOM), benzyloxymethyl (BOM), tetrahydropyranyl (THP), benzyl (Bn), benzoyl (Bz), p-methoxybenzyl (PMB), p-nitrobenzyl, o-nitrobenzyl, p-nitrobenzoyl (PNB), trimethylsilyl (TMS) and the like.

Unless otherwise specified the term '$C_1$-$C_5$ alkoxy' represents methoxy, ethoxy, isopropoxy, butyloxy and pentyloxy.

Unless otherwise specified the term 'halo' represents fluoro, chloro, bromo or iodo.

The aforementioned process involves reaction of compound of Formula XI with a compound of Formula IVa or a salt thereof in presence of a suitable base and in a suitable solvent to obtain a compound of Formula VI; wherein when 'X' is halo, then '$R_1$' is either hydrogen or a suitable protecting group; and when 'X' is nitro, then '$R_1$' is hydrogen.

In a preferred embodiment the exemplary compound of Formula XI, Formula IVa and Formula VI can be represented as follows:

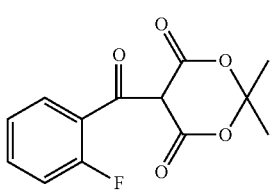

Formula XIa

-continued

Formula XIb

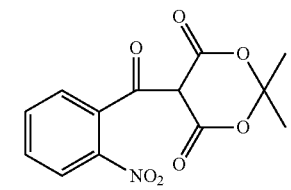

Formula IV

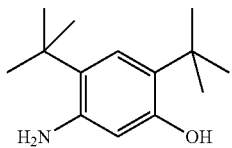

Formula VIa

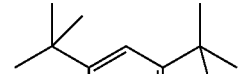

Formula VIb

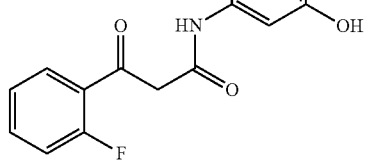

Formula VIp'

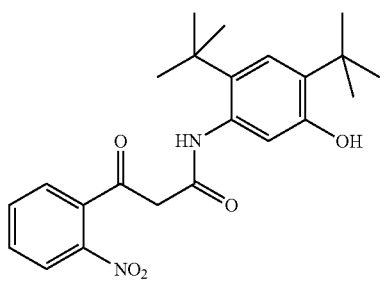

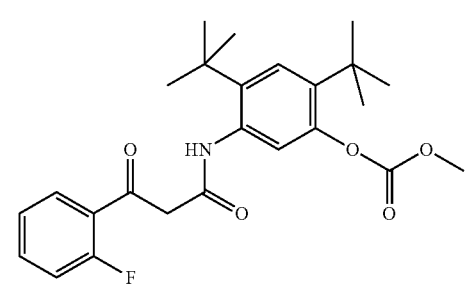

The compound of Formula XIa and compound of Formula IVa or a salt thereof known in the art and can be prepared by any method known in the art, for example compound of Formula XI may be prepared by the process disclosed in *Archiv der Pharmazie*, 2013, vol 346, 7, page 521-533 or by the process described in below examples; and compound of Formula IVa or a salt can be prepared by using the process disclosed in applicant's PCT application No. 2016/075703.

Exemplary bases used herein for the reaction of a compound of Formula XIa or Formula XIb with a compound of Formula IV or a salt thereof, includes but are not limited to inorganic bases such as sodium hydroxide, potassium hydroxide, sodium methoxide, sodium ethoxide, sodium tert-butoxide, potassium tert-butoxide, sodium carbonate, potassium carbonate, cesium carbonate, sodium bicarbonate, potassium bicarbonate, organic bases such as triethylamine, isopropylethylamine, diisopropylamine, diisopropylethylamine, N-methylmorpholine, piperidine, pyridine and the like and mixtures thereof; preferably diisopropylethylamine.

The suitable solvent for the reaction of a compound of Formula XIa or Formula XIb with a compound of Formula IV or a salt thereof, include but is not limited to amides, halogenated hydrocarbons, aromatic hydrocarbons and mixtures thereof. The amides include, but are not limited to dimethyl formamide, dimethyl acetamide, N-methyl pyrrolidinone and the like; halogenated hydrocarbons include, but are not limited to methylene chloride, ethylene chloride and the like; aromatic hydrocarbons include, but are not limited to toluene, xylene and the like and mixtures thereof; preferably toluene.

The reaction of Formula XIa or Formula XIb with a compound of Formula IV or a salt is advantageously carried out at a temperature of about room temperature to reflux temperature; preferably at 90° C. to about 110° C.

The resultant compound of Formula VI (preferably Formula VIa, Formula VIp' or Formula VIb) can be isolated by conventional methods; for example concentration of the reaction mass under reduced pressure to obtain solid compound as crude, which can be optionally separated by adding suitable hydrocarbon solvent such as hexane, heptane, cyclohexane and the like; preferably heptane and then filtering the product.

In another embodiment, the present invention provides a process for the preparation of compound of Formula VI, comprising: reacting the compound of Formula XII with a compound of Formula IVa or a salt thereof to obtain a compound of Formula VI, Formula XII

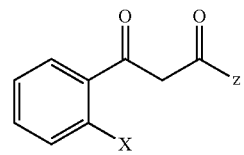

Formula IVa

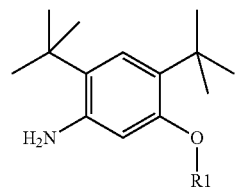

Formula VI

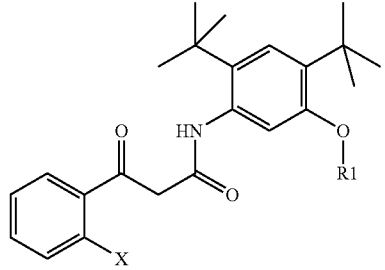

wherein when 'X' is halo, then '$R_1$' is either hydrogen or a suitable protecting group; when 'X' is nitro, then '$R_1$' is hydrogen; and wherein "Z" represents $C_1$-$C_5$ alkoxy or halogen.

The aforementioned process involves reaction of compound of Formula XII with a compound of Formula IVa or a salt thereof in presence of a suitable base and in a suitable solvent to obtain a compound of Formula VI.

In a preferred embodiment the exemplary compound of Formula XII, Formula IVa and Formula VI can be represented as follows:

Formula XIIa

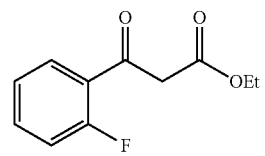

Formula XIIb

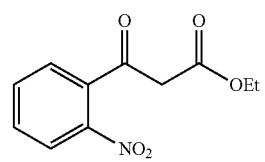

Formula IV

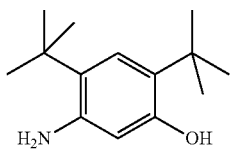

Formula VIa

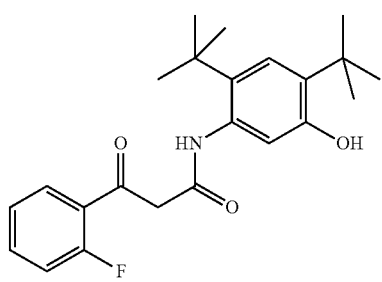

Formula VIb

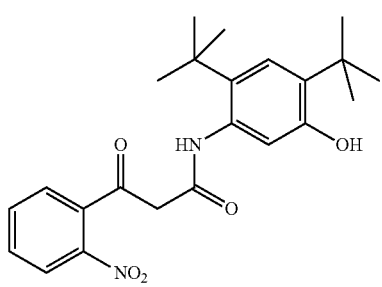

Formula VIp'

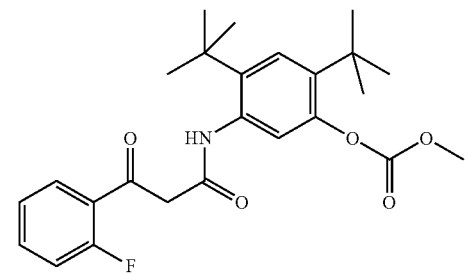

The compound of Formula XII is known in the art and can be prepared by any method known in the art, for example may be prepared by the process disclosed in *Journal of Heterocyclic Chemistry,* 2011, vol 48, 3, page 620-625, *Bioorganic and Medicinal Chemistry,* 2013, vol 21, 11, page 2843-2855 or by the process described in below examples.

The base and solvent used herein for reaction of compound of Formula XIIa or Formula XIIb with a compound of Formula IV or a salt thereof is same as used for the reaction of compound of Formula XIa or Formula XIb with a compound of Formula IV or a salt thereof as mentioned above.

The reaction of Formula XIIa or Formula XIIb with a compound of Formula IV or a salt is advantageously carried out at a temperature of about room temperature to reflux temperature; preferably at 90° C. to about 110° C.

The resultant compound of Formula VI (preferably Formula VIa, Formula VIp' or Formula VIb) can be isolated by conventional methods; for example concentration of the reaction mass under reduced pressure to obtain solid compound as crude, which can be optionally separated by adding suitable hydrocarbon solvent such as hexane, heptane, cyclohexane and the like; preferably heptane and then filtering the product.

The compound of Formula VI, preferably a compound of Formula VIa, Formula VIp' or Formula VIb obtained by the processes described just as above can be used as intermediate in the preparation of ivacaftor of the invention.

In another embodiment, the present invention provides a process for the preparation of ivacaftor of Formula I or a pharmaceutically acceptable salt thereof: comprising:

a2) reacting a compound of Formula VIb with dimethyl formamide-dimethyl amine complex to obtain a compound of Formula VIIb, Formula VIb

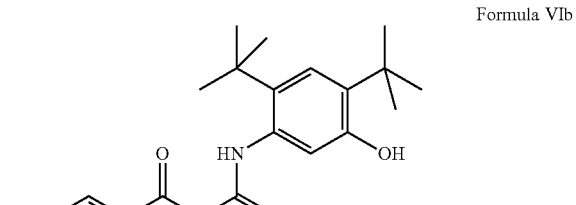

Formula VIIb

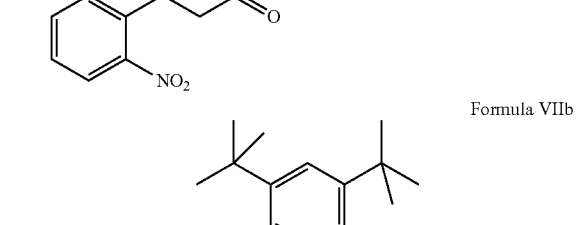

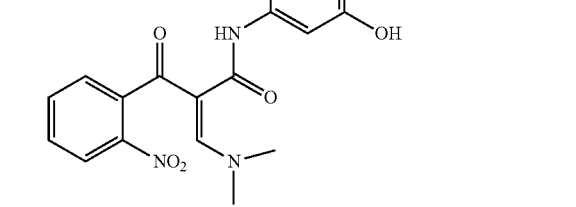

b2) reducing the compound of Formula VIIb in presence of a suitable reducing agent to obtain a compound of Formula X, and

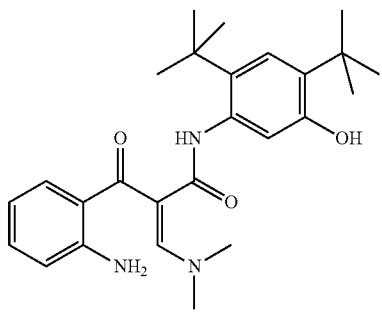

Formula X c2) converting the compound of Formula X in to ivacaftor.

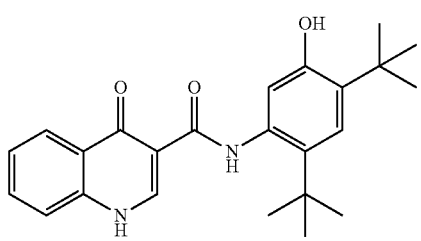

Formula I

The compound of Formula VIb may be prepared by the processes described as above of the present invention.

The step a2) of the aforementioned process involves reaction of compound of Formula VIb with dimethyl formamide-dimethyl amine complex to obtain a compound of Formula VIIb is same as the process described for the preparation of compound of Formula VIIa. The step b2) of the aforementioned process involves reduction of the compound of Formula VIIb in presence of a suitable reducing agent to obtain a compound of Formula X.

The suitable reducing agent used herein is selected from the group consisting of Fe/ammonium chloride, Fe/ammonium formate, Fe/HCl, hydrogen gas, palladium on carbon, raney nickel, platinum oxide, sodium hydrosulfite, zinc and the like; preferably Fe/ammonium chloride.

The reduction of the compound of Formula VIIb is carried out in a suitable solvent. The suitable solvent includes but is not limited to ethers, alcohols, amides, sulfoxides, water and mixtures thereof. Preferably ethers include, but are not limited to tetrahydrofuran, 2-methyltetrahydrofuran, dimethyl ether, methyl tertiary butyl ether and the like; alcohols include, but are not limited to methanol, ethanol, isopropanol and the like; amides include, but are not limited to dimethylformamide, dimethyl acetamide, N-methyl pyrrolidinone and the like; sulfoxides include, but are not limited to dimethylsulfoxide, sulfolane and the like; water and mixtures thereof; preferably ethanol.

The reduction of the compound of Formula VIIb advantageously carried out at a temperature of about room temperature to reflux temperature; preferably at 55° C. to about 80° C.

The step c2) of the aforementioned process involves convertion of the compound of Formula X in to ivacaftor.

In an embodiment, the process of step c2) of conversion of the compound of Formula X in to ivacaftor is carried out incisively without isolating the compound of Formula X.

In another embodiment, the present invention provides a compound of Formula VI or a pharmaceutically acceptable salt thereof.

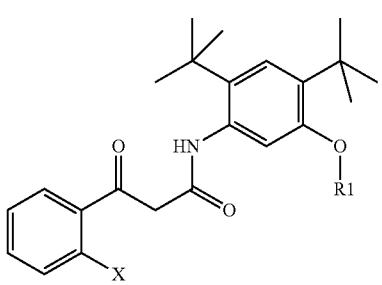

Formula VI wherein 'X' represents halo and '$R_1$' represents either hydrogen or a suitable protecting group.

In another embodiment, the present invention provides a compound of Formula VIp or a pharmaceutically acceptable salt thereof.

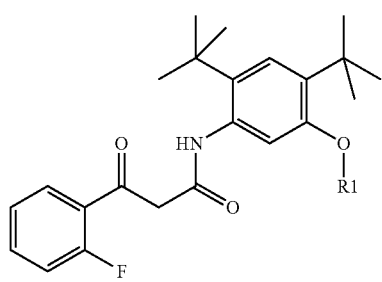

Formula VIp wherein '$R_1$' represents either hydrogen or a suitable protecting group.

In another embodiment, the present invention provides a compound of Formula VIa a pharmaceutically acceptable salt thereof.

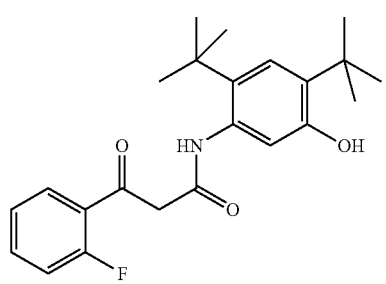

Formula VIa

In another embodiment, the present invention provides a compound of Formula VIp' or a pharmaceutically acceptable salt thereof.

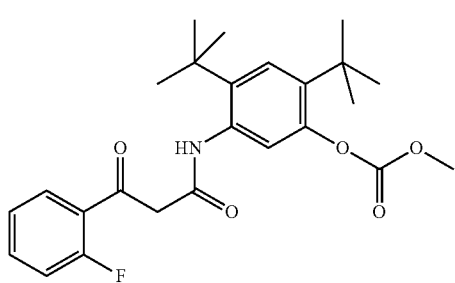

Formula VIp'

In another embodiment, the present invention provides a compound of Formula VIb or a pharmaceutically acceptable salt thereof.

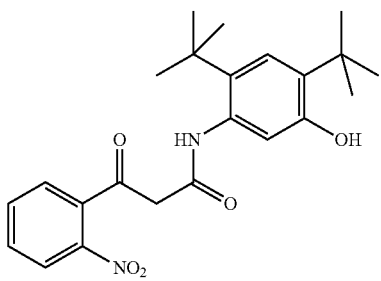

Formula VIb

In another embodiment, the present invention provides a compound of Formula VII or a pharmaceutically acceptable salt thereof.

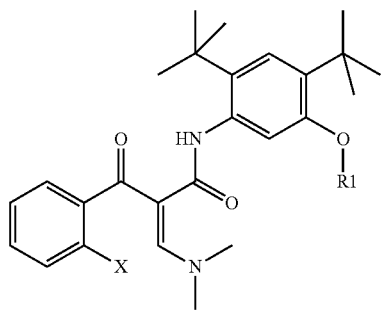

Formula VII wherein 'X' represents halo and '$R_1$' represents either hydrogen or a suitable protecting group.

In another embodiment, the present invention provides a compound of Formula VIIp or a pharmaceutically acceptable salt thereof.

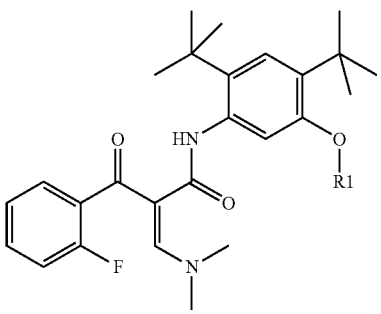

Formula VIIp wherein '$R_1$' represents either hydrogen or a suitable protecting group.

In another embodiment, the present invention provides a compound of Formula VIIa or a pharmaceutically acceptable salt thereof.

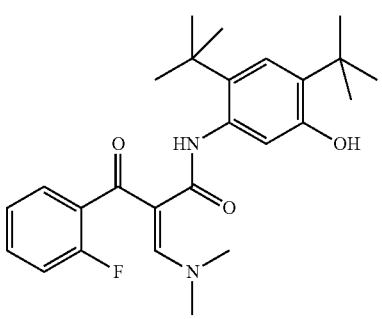

Formula VIIa

In another embodiment, the present invention provides a compound of Formula VIIp' or a pharmaceutically acceptable salt thereof.

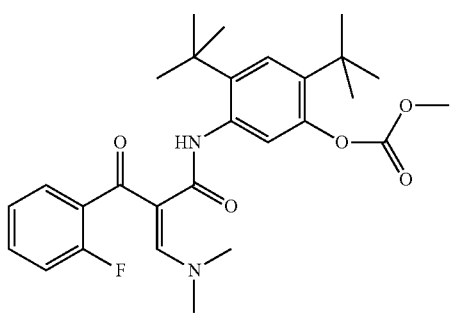

Formula VIIp'

In another embodiment, the present invention provides a compound of Formula VIIb or a pharmaceutically acceptable salt thereof.

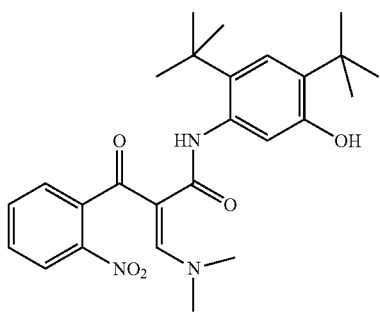

Formula VIIb

In another embodiment, the present invention provides a compound of Formula VIII or a pharmaceutically acceptable salt thereof.

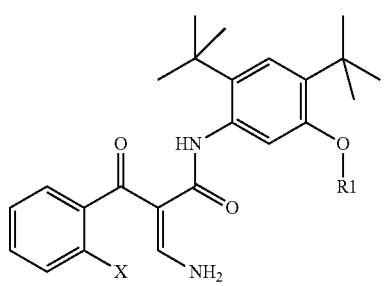

Formula VIII wherein 'X' represents halo and 'R₁' represents either hydrogen or a suitable protecting group.

In another embodiment, the present invention provides a compound of Formula VIIIp or a pharmaceutically acceptable salt thereof.

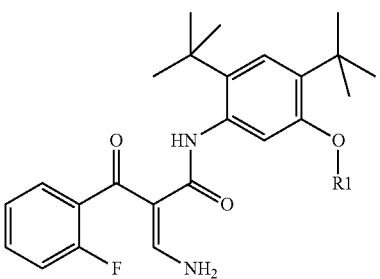

Formula VIIIp wherein 'R₁' represents either hydrogen or a suitable protecting group.

In another embodiment, the present invention provides a compound of Formula VIIIa or a pharmaceutically acceptable salt thereof.

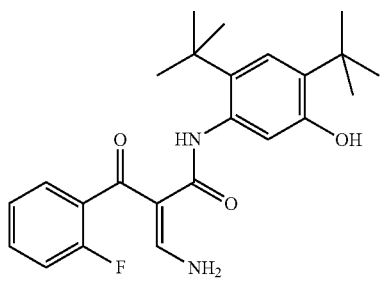

Formula VIIIa

In another embodiment, the present invention provides a compound of Formula VIIIp' or a pharmaceutically acceptable salt thereof.

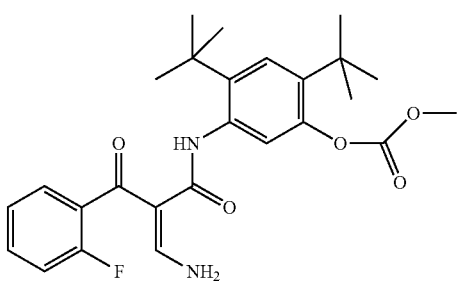

Formula VIIIp'

In another embodiment, the present invention provides a compound of Formula Xp or a pharmaceutically acceptable salt thereof.

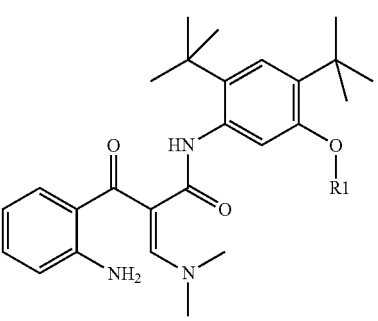

Formula Xp wherein 'R₁' represents either hydrogen or a suitable protecting group.

In another embodiment, the present invention provides a compound of Formula X or a pharmaceutically acceptable salt thereof.

Formula X

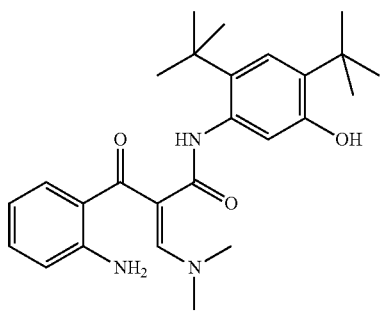

In another embodiment, the present invention provides a compound of Formula Xp' or a pharmaceutically acceptable salt thereof.

Formula Xp'

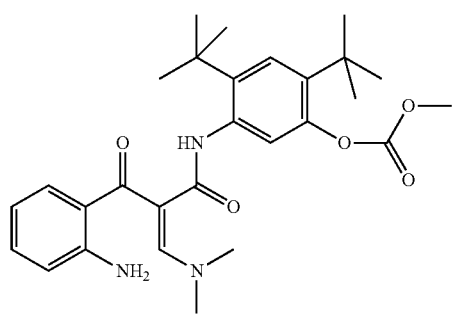

In another embodiment, the present invention provides a process for the preparation of ivacaftor of Formula I or a pharmaceutically acceptable salt thereof:

Formula I

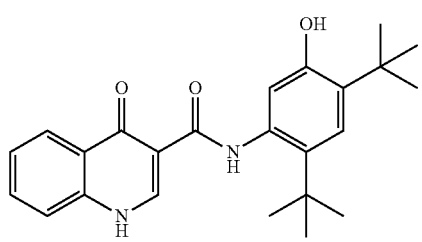

comprising:
  a5) reacting a compound of Formula VI with ($C_{1-5}$ alkyl)$_3$-orthoformate to obtain a compound of Formula XIII, Formula VI

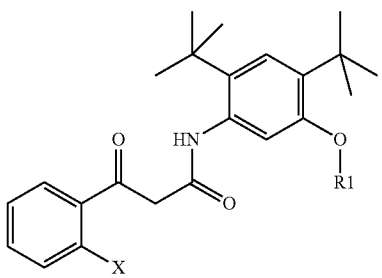

Formula XIII

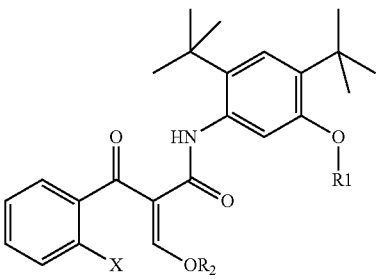

wherein 'X' represents halo; '$R_1$' represents either hydrogen or a suitable protecting group; and '$R_2$' represents $C_{1-5}$ alkyl;
  b5) reacting the compound of Formula XIII with a source of ammonia to obtain a compound of Formula VIII, and Formula VIII

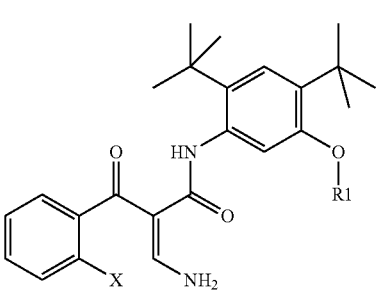

c5) cyclizing the compound of Formula VIII to obtain ivacaftor, when $R_1$ is hydrogen, or to obtain a compound of Formula IX, when $R_1$ is a protecting group and deprotecting the Formula IX to obtain ivacaftor.

Formula IX

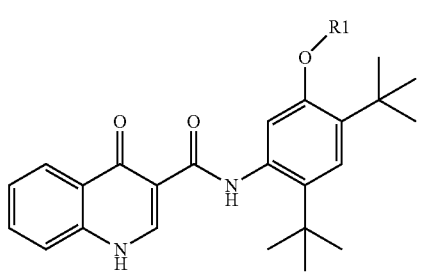

Unless otherwise specified the term suitable hydroxy protecting group used herein are selected from methoxycarbonyl, methoxymethyl (MOM), benzyloxymethyl (BOM), tetrahydropyranyl (THP), benzyl (Bn), benzoyl (Bz), p-methoxybenzyl (PMB), p-nitrobenzyl, o-nitrobenzyl, p-nitrobenzoyl (PNB), trimethylsilyl (TMS) and the like.

Unless otherwise specified the term 'halo' represents fluoro, chloro, bromo or iodo.

Unless otherwise specified the term 'suitable leaving group' represents halogen such as fluoro, chloro, bromo, iodo or mesyl, tosyl and the like.

Unless otherwise specified the term '$C_{1-5}$ alkyl' represents methyl, ethyl, propyl, butyl and pentyl.

The compound of Formula VI (preferably Formula VIa or Formula VIb) can be prepared by using the process disclosed in applicant's PCT application No. 2016/075730.

In a preferred embodiment the exemplary compound of Formula VI can be represented as follows:

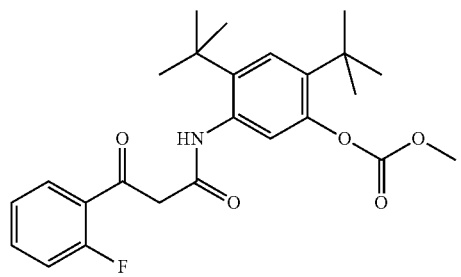

Formula VIp

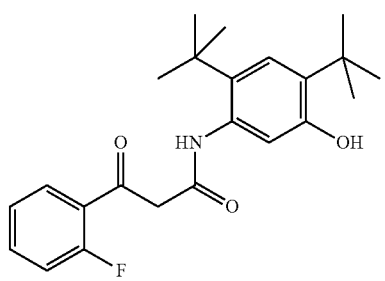

Formula VIa

The step a5) of the aforementioned process involves reaction of compound of Formula VI with ($C_{1-5}$ alkyl)$_3$-orthoformate in presence of a suitable Lewis acid; wherein 'X' represents halo and '$R_1$' represents either hydrogen or a suitable protecting group to obtain a compound of Formula XIII.

In a further preferred embodiment the exemplary compound of Formula XIII can be represented as follows:

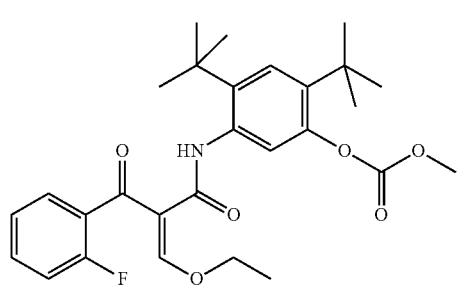

Formula XIIIp

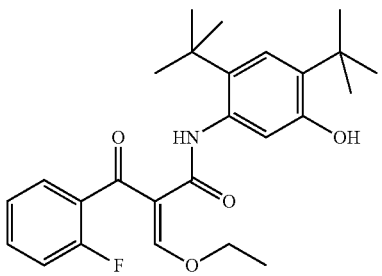

Formula XIIIa

The suitable ($C_{1-5}$ alkyl)$_3$-orthoformate used herein for step a5) includes but is not limited to trimethyl orthoformate, triethyl orthoformate, tripropyl orthoformate, tributyl orthoformate, tripentyl orthoformate and the like; preferably triethyl orthoformate.

The suitable Lewis acid used herein for step a5) includes but is not limited to zinc chloride, tin(IV) chloride, tin(II) chloride, aluminium chloride, boron trifluoride and the like; preferably zinc chloride.

The reaction of compound of Formula VI with ($C_{1-5}$ alkyl)$_3$-orthoformate may be optionally carried out in a suitable solvent, which includes but is not limited to acid anhydride, nitriles, ethers, aromatic hydrocarbons and mixtures thereof. The acid anhydride include, but are not limited to acetic anhydride, propionic anhydride and the like; nitriles include, but are not limited to acetonitrile, propionitrile and the like; ethers include, but are not limited to tetrahydrofuran, dimethyl ether, methyl tertiary butyl ether, dimethoxyethane and the like; aromatic hydrocarbons include, but are not limited to toluene, xylene and the like and mixtures thereof; preferably acetic anhydride.

The reaction of compound of Formula VI with ($C_5$ alkyl)$_3$-orthoformate advantageously carried out at a temperature of about room temperature to reflux temperature; preferably at 20° C. to about 40° C.

After completion of the reaction, the resultant compound of Formula XIII may be isolated by known techniques, for example the reaction mass containing compound of Formula XIII may be quenched with water followed by extracting the product with a suitable water immiscible solvent such as ethyl acetate, methylene chloride or toluene; preferably ethyl acetate and then evaporating the solvent completely under normal or reduced pressure to obtain a compound of Formula XIII.

The step b5) of the aforementioned process involves reaction of the compound of Formula XIII with a source of ammonia to obtain a compound of Formula VIII, wherein 'X' and '$R_1$' are defined as above.

In a preferred embodiment the exemplary compound of Formula VIII can be represented as follows:

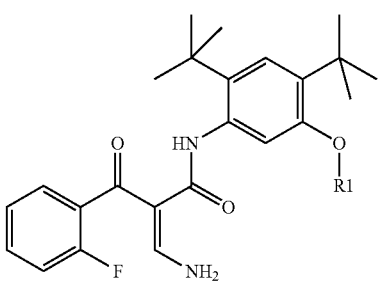

Formula VIIIp wherein 'R₁' represents either hydrogen or a suitable protecting group.

In a further preferred embodiment the exemplary compound of Formula VIII can be represented as follows:

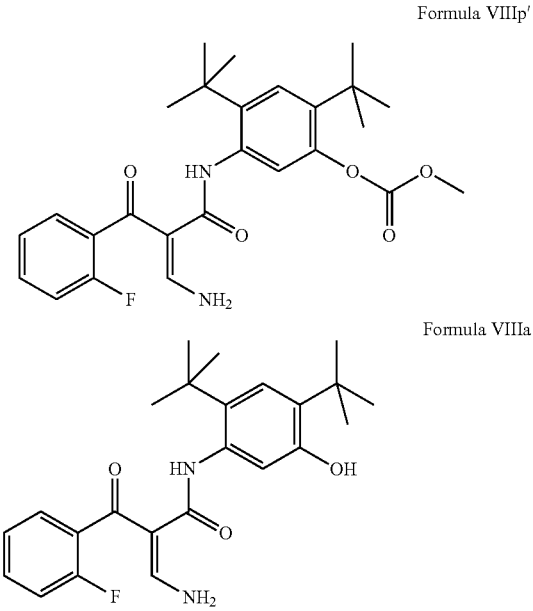

Formula VIIIp′

Formula VIIIa

Exemplary sources of ammonia used herein for the reaction of compound of Formula XIII includes but is not limited to ammonia gas, ammonium hydroxide, ammonium acetate, ammonium formate and the like; preferably ammonium hydroxide.

The reaction of the compound of Formula XIII with a source of ammonia may be carried out in a suitable solvent. The suitable solvent includes but is not limited to alcohols, amides, aromatic hydrocarbons, water and mixtures thereof. The alcohols include, but are not limited to methanol, ethanol, isopropanol and the like; amides include, but are not limited to dimethyl formamide, dimethyl acetamide, N-methyl pyrrolidinone and the like; aromatic hydrocarbons include, but are not limited to toluene, xylene and the like; water and mixtures thereof; preferably ethanol.

The reaction of the compound of Formula XIII with a source of ammonia advantageously carried out at a temperature of about room temperature to reflux temperature; preferably at 70° C. to about 80° C.

The resultant compound of Formula VIII obtained after step b5) reaction may be converted in to ivacaftor without isolating the Formula VIII or alternatively the compound of Formula VIII may be isolated as solid by known methods.

The step c5) of the aforementioned process involves cyclization of the compound of Formula VIII to obtain ivacaftor, when R₁ is hydrogen, or to obtain a compound of Formula IX, when R₁ is a protecting group and deprotecting the Formula IX to obtain ivacaftor.

The cyclization of compound of Formula VIII is carried out in presence of a suitable base to obtain a compound of Formula IX. The suitable base includes but is not limited to inorganic bases such as sodium hydroxide, potassium hydroxide, sodium methoxide, sodium ethoxide, sodium tert-butoxide, potassium tert-butoxide, sodium carbonate, potassium carbonate, cesium carbonate, sodium bicarbonate, potassium bicarbonate, organic bases such as triethylamine, isopropylethylamine, diisopropylamine, diisopropylethylamine, N-methylmorpholine, piperidine, pyridine and the like and mixtures thereof; preferably potassium carbonate.

The cyclization of compound of Formula VIII is carried out in a suitable solvent. The suitable solvent includes but is not limited to ethers, alcohols, aromatic hydrocarbons, amides, sulfoxides, nitriles and mixtures thereof. Preferably ethers include, but are not limited to tetrahydrofuran, 2-methyl tetrahydrofuran, dimethyl ether, methyl tertiary butyl ether and the like; alcohols include, but are not limited to methanol, ethanol, isopropanol and the like; aromatic hydrocarbons include, but are not limited to toluene, xylene and the like; amides include, but are not limited to dimethylformamide, dimethyl acetamide, N-methyl pyrrolidinone and the like; sulfoxides include, but are not limited to dimethylsulfoxide, sulfolane and the like; nitriles include, but are not limited to acetonitrile, propionitrile and like and mixtures thereof; preferably dimethylformamide.

The deprotection of the compound of Formula IX is carried out in presence of a suitable deprotecting agent and a suitable solvent.

The suitable deprotecting agent used herein for the deprotection of the compound of Formula IX; wherein 'R₁' defined as above includes but is not limited to acid deprotecting agent such as hydrochloric acid, hydrobromic acid, trifluoro acetic acid and the like and mixture thereof; base deprotecting agent such as potassium carbonate, sodium hydroxide, sodium ethoxide and the like and mixture thereof; preferably potassium carbonate.

The suitable solvent for deprotection of the compound of Formula IX; wherein 'R₁' defined as above includes but is not limited to alcohols, ketones, ethers, amides, sulfoxides and mixtures thereof. The alcohols include, but are not limited to methanol, ethanol, isopropanol and the like; ketones include, but are not limited to acetone, methyl isobutyl ketone, methyl ethyl ketone and the like; ethers include, but are not limited to tetrahydrofuran, 2-methyl tetrahydrofuran, methyl tertiary butyl ether and the like; amides include, but are not limited to dimethyl formamide, dimethyl acetamide, N-methyl pyrrolidinone and the like; sulfoxides include, but are not limited to dimethylsulfoxide, sulfolane and the like; and mixture thereof; preferably dimethylformamide.

The deprotection reaction may be carried out at a temperature of about 0° C. to reflux temperature; preferably at 90° C. to about 110° C.

After completion of the deprotection reaction, the resultant ivacaftor of Formula I can be isolated by known isolation techniques, for example the resultant reaction mass may be adjusted pH to about 2.0 to 2.5 with a suitable acid such as hydrochloric acid, sulfuric acid, phosphoric acid, acetic acid and the like, followed by precipitated solid compound can be separated by filtration and the solid ivacaftor obtained may be optionally purification from a suitable solvent such as methanol, ethanol and the like.

In another embodiment, the present invention provides a process for the preparation of ivacaftor of Formula I or a pharmaceutically acceptable salt thereof: comprising:

a6) reacting a compound of Formula VIb with ($C_{1-5}$ alkyl)₃-orthoformate to obtain a compound of Formula XIV, wherein 'R₂' represents $C_{1-5}$ alkyl,

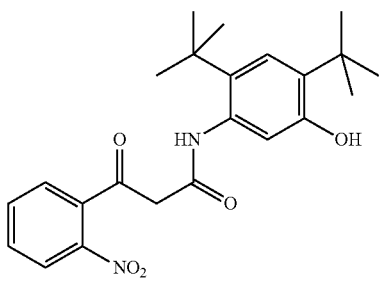

Formula VIb

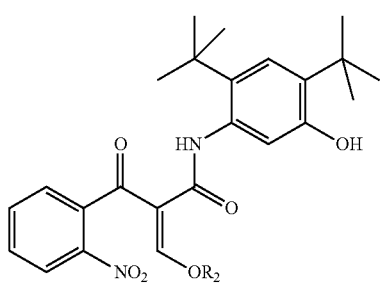

Formula XIV b6) reducing the compound of Formula XIV in presence of a suitable reducing agent to obtain a compound of Formula XV, and

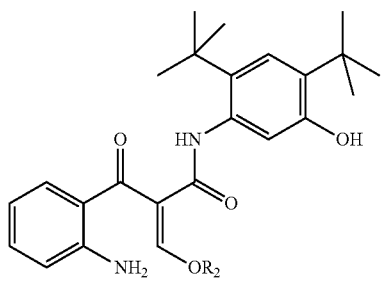

Formula XV c6) cyclizing the compound of Formula XV in to ivacaftor.

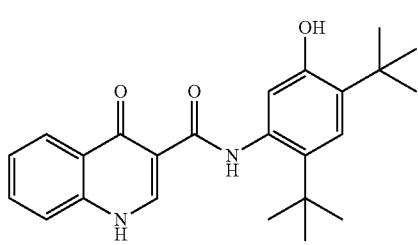

Formula I

The step a6) of the aforementioned process involves reaction of compound of Formula VIb with $(C_{1-5}$ alkyl$)_3$-orthoformate to obtain a compound of Formula XIV is same as the process described for the preparation of compound of Formula VIIa or Formula VIIb.

The step b6) of the aforementioned process involves reduction of the compound of Formula XIV in presence of a suitable reducing agent to obtain a compound of Formula XV.

The suitable reducing agent used herein is selected from the group consisting of Fe/ammonium chloride, Fe/ammonium formate, Fe/HCl, hydrogen gas, Palladium on carbon, Raney nickel, Platinum oxide, Sodium hydrosulfite, Zinc and the like; preferably Fe/ammonium chloride.

The reduction of the compound of Formula XIV is carried out in a suitable solvent. The suitable solvent includes but is not limited to ethers, alcohols, amides, sulfoxides, water and mixtures thereof. Preferably ethers include, but are not limited to tetrahydrofuran, 2-methyltetrahydrofuran, dimethyl ether, methyl tertiary butyl ether and the like; alcohols include, but are not limited to methanol, ethanol, isopropanol and the like; amides include, but are not limited to dimethylformamide, dimethylsulfoxide, dimethyl acetamide, N-methyl pyrrolidinone and the like; sulfoxides include, but are not limited to dimethylsulfoxide, sulfolane and the like; water and mixtures thereof; preferably ethanol.

The reduction of the compound of Formula XIV advantageously carried out at a temperature of about room temperature to reflux temperature; preferably at 60° C. to about 80° C.

The step c6) of the aforementioned process involves cyclization of the compound of Formula XV in to ivacaftor.

In an embodiment, the process of step c6) of cyclization of the compound of Formula XV in to ivacaftor is carried out without isolating the compound of Formula XV.

In another embodiment, the present invention provides a process for the preparation of ivacaftor of Formula I or a pharmaceutically acceptable salt thereof; comprising:

a7) reacting a compound of Formula XVI with a compound of Formula IVa or a salt thereof to obtain a compound of Formula XVII,

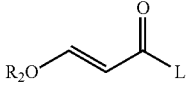

Formula XVI

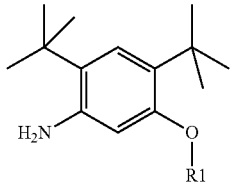

Formula IVa

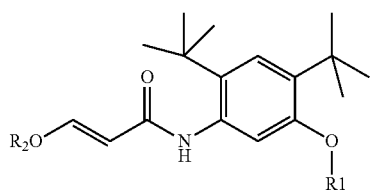

Formula XVII b7) reacting the compound of Formula XVII with a compound of Formula XVIII to obtain a compound of Formula XIII, and

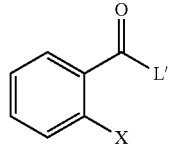

Formula XVIII

Formula XIII

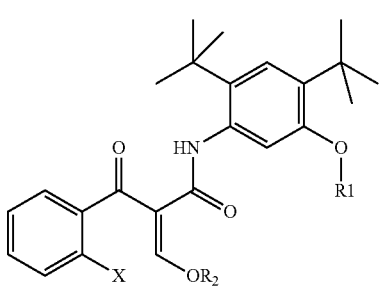

c7) converting the compound of Formula XIII in to ivacaftor; wherein 'X' represents halo or nitro; 'R₁' represents either hydrogen or a suitable protecting group; 'R₂' represents $C_{1-5}$ alkyl; L and L' represents a suitable leaving group.

The compound of Formula XVI or a salt thereof known in the art and can be prepared by any process known in the art or by using the process disclosed in applicant's PCT application No. 2016/075703 or by using the process disclosed in examples.

The step a7) of aforementioned process involves reaction of compound of Formula XVI with a compound of Formula IVa or a salt thereof in presence of a suitable base and in a suitable solvent to obtain a compound of Formula XVII, wherein 'R₂' represents $C_{1-5}$ alkyl; L and L' represents a suitable leaving group.

In a preferred embodiment the exemplary compound of Formula XVI, Formula IVa and Formula XVII can be represented as follows:

Formula XVIa

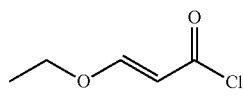

Formula IVp

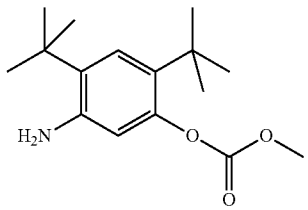

Formula IV

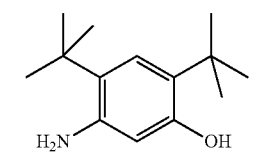

Formula XVIIa

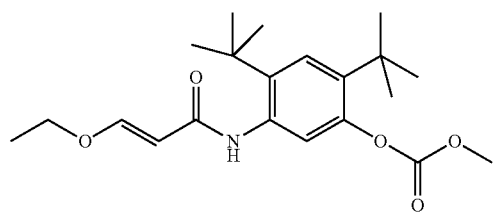

Formula XVIIb

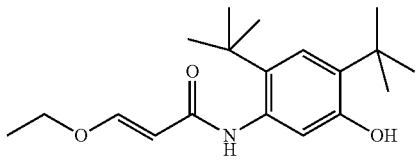

Exemplary bases used herein for the reaction of a compound of Formula XVI with a compound of Formula IVa or a salt thereof, includes but are not limited to inorganic bases such as sodium hydroxide, potassium hydroxide, sodium methoxide, sodium ethoxide, sodium tert-butoxide, potassium tert-butoxide, sodium carbonate, potassium carbonate, cesium carbonate, sodium bicarbonate, potassium bicarbonate, organic bases such as triethylamine, isopropylethylamine, diisopropylamine, diisopropylethylamine, N-methylmorpholine, piperidine, pyridine and the like and mixtures thereof; preferably pyridine.

The suitable solvent for the reaction of a compound of Formula XVI with a compound of Formula IVa or a salt thereof, include but is not limited to amides, halogenated hydrocarbons, aromatic hydrocarbons and mixtures thereof. The amides include, but are not limited to dimethyl formamide, dimethyl acetamide, N-methyl pyrrolidinone and the like; halogenated hydrocarbons include, but are not limited to methylene chloride, ethylene chloride and the like; aromatic hydrocarbons include, but are not limited to toluene, xylene and the like and mixtures thereof; preferably methylene chloride.

The reaction of Formula XVI with a compound of Formula IVa or a salt thereof is advantageously carried out at a temperature of about room temperature to reflux temperature; preferably at 20° C. to about 40° C.

The step b7) of the aforementioned process involves reaction of the compound of Formula XVII with a compound of Formula XVIII in presence of a suitable base and in a suitable solvent to obtain a compound of Formula XIII, wherein 'R1', 'R2', 'X', L and L' are defined as above.

In a preferred embodiment the exemplary compound of Formula XVIII can be represented as follows:

Formula XVIIIa

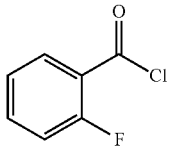

Formula XVIIIb

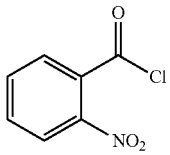

The base and solvent used herein for reaction of compound of Formula XVII with a compound of Formula XVIII is same as used for the reaction of compound of Formula XVI with a compound of Formula IVa or a salt thereof as mentioned above.

The reaction of Formula XVII with a compound of Formula XVIII is advantageously carried out at a temperature of about room temperature to reflux temperature; preferably at 40° C. to about 65° C.

The resultant compound of Formula XIII can be isolated by conventional methods; for example washing the reaction mass with a suitable aqueous base such as sodium bicarbonate, potassium bicarbonate and the like. Then the product containing solvent may be separated and subjected to evaporation under vacuum to obtain solid compound as crude, which can be optionally separated by adding suitable hydrocarbon solvent such as hexane, heptane, cyclohexane and the like; preferably heptane and then filtering the product.

The compound of Formula XIII obtained by the processes described just as above can be used as intermediate in the preparation of ivacaftor of the invention.

The step c7) of the aforementioned process involves convertion of the compound of Formula XIII in to ivacaftor by the process same as described above.

In another embodiment, the present invention provides a compound of Formula XIII or a pharmaceutically acceptable salt thereof:

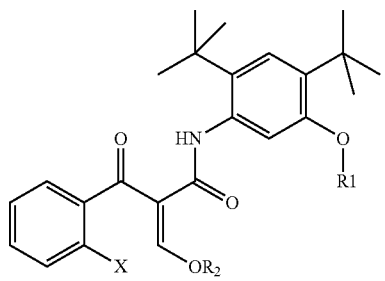

Formula XIII wherein 'X' represents Halo, —NO$_2$ or —NH$_2$, 'R$_1$' represents either hydrogen or a suitable protecting group; and 'R$_2$' represents C$_{1-5}$ alkyl; provided that wherein when "X" is —NO$_2$ or —NH$_2$ then 'R$_1$' is hydrogen.

In another embodiment, the present invention provides a compound of Formula XIIIa or a pharmaceutically acceptable salt thereof.

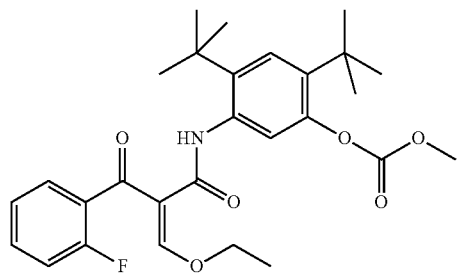

Formula XIIIp

In another embodiment, the present invention provides a compound of Formula XIIIb or a pharmaceutically acceptable salt thereof.

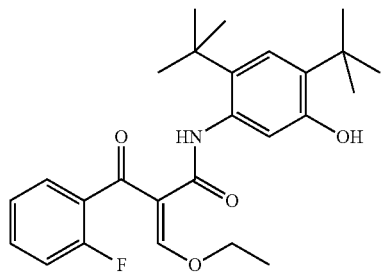

Formula XIIIa

In another embodiment, the present invention provides a compound of Formula XIIIb, wherein 'R$_2$' represents C$_{1-5}$ alkyl, or a pharmaceutically acceptable salt thereof.

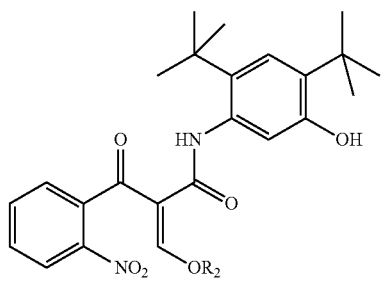

Formula XIIIb

In another embodiment, the present invention provides a compound of Formula XV, wherein 'R$_2$' represents C$_{1-5}$ alkyl, or a pharmaceutically acceptable salt thereof.

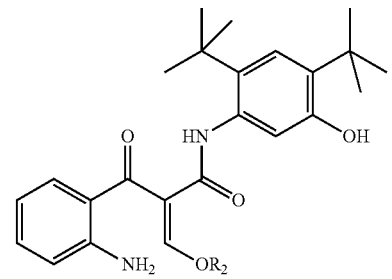

Formula XV

In another embodiment, the present invention provides ivacaftor or a pharmaceutically acceptable salt thereof obtained by the processes described herein, having a purity of at least about 97%, as measured by HPLC, preferably at least about 98% as measured by HPLC, and more preferably at least about 99.5%, as measured by HPLC.

As used herein, the pharmaceutical acceptable salts include acid addition salts formed with inorganic acids or with organic acids. The inorganic acids may be selected from hydrochloric acid, hydrobromic acid, sulfuric acid, phosphoric acid, nitric acid, sulfamic acid, and the like; organic acids may be selected from acetic acid, oxalic acid, fumaric acid, citric acid, succinic acid, tartaric acid, salicylic acid, benzoic acid, glycolic acid, methane sulfonic acid, ethanesulfonic acid, benzenesulfonic acid, p-toluenesulfonic acid, lactic acid, maleic acid, malonic acid, malic acid and the like.

In another embodiment, the present invention provides a pharmaceutical composition, comprising ivacaftor or a pharmaceutically acceptable salt thereof prepared by the processes of the present invention and at least one pharmaceutically acceptable excipient. Such pharmaceutical composition may be administered to a mammalian patient in any dosage form, e.g., solid, liquid, powder, injectable solution, etc.

EXAMPLES

The following non limiting examples illustrate specific embodiments of the present invention. They are not intended to be limiting the scope of the present invention in any way.

Example—1: Preparation of Ivacaftor 4-oxo-1,4-dihydroquinoline-3-carboxylic acid (5 g), methylene chloride (100 ml) and triethylamine (5.35 g) were charged into a round bottom flask at 25-35° C. stirred at for 10 min at same temperature. Reactions mass was cooled to 0-5° C., slowly add thionyl chloride (6.30 g) over a period of 15 min, then the reaction mass was heated to reflux and maintained for 2 to 3 hrs. After completion of the reaction, reaction mass was distilled completely under vacuum at below 40° C. and co-distilled with methylene chloride (2×50 ml). Reaction mass was cooled to room temperature and diluted with methylene chloride (50 ml) further cooled to 0-5° C. To the reaction mass was charged solution of 5-amino-2,4-di-tert-butyl phenol hydrochloride (8.2 g) in methylene chloride (50 ml) and triethylamine (5.35 g) at 0-5° C. Reaction mass was heated to 25-35° C. and stirred for 4 to 6 hrs. After completion of the reaction, reaction mass was distilled completely under vacuum at below 40° C. and to the resultant reaction ethyl acetate (100 ml) was charged and washed with 5% sodium carbonate(2×50 ml), water (50 ml), 1% aq.HCl solution (50 ml) and water (50 ml) and the resultant organic layer was distilled completely u/v and co-distilled with ethanol to obtain crude. The obtaine crude was dissolved in ethanol (450 ml) at reflux temperature and then distilled the resultant reaction mass upto ~20 vol at 40° C. Reaction mass was cooled to 25-35° C. then filtered the solid and washed with ethanol (10 ml). The resulting wet cake was dried under vacuum at 60-65° C. to obtain Ivacaftor. Yield: 5.0 g.

Example—2: Preparation of N-(2,4-di-tert-butyl-5-hydroxyphenyl)-1-benzyl-4-oxo-1,4-dihydroquinoline-3-carboxamide N-Benzyl-4-oxo-1,4-dihydroquinoline-3-carboxylic acid (3 g), methylene chloride (60 ml) and triethylamine (2.17 g) were charged in to a round bottom flask at 25-35° C. and stirred for 10 min at same temperature. Reactions mass was cooled to 0-5° C., slowly add thionyl chloride (2.55 g) over a period of 15 min, then the reaction mass was heated to reflux and maintained for 2 to 3 hrs. After completion of the reaction, reaction mass was distilled completely under vacuum at below 40° C. and co-distilled with methylene chloride (2×30 ml). Reaction mass was cooled to room temperature and diluted with methylene chloride (30 ml) further cooled to 0-5° C. To the reaction mass was charged solution of 5-amino-2,4-di-tert-butyl phenol hydrochloride (3.32 g) in methylene chloride (30 ml) and triethylamine (2.17 g) at 0-5° C. Reaction mass was heated to 25-35° C. and stirred for 4 to 6 hrs. After completion of the reaction, reaction mass was distilled completely under vacuum at below 40° C. and to the resultant reaction ethyl acetate (60 ml) was charged and washed with 5% sodium carbonate(2×30 ml), water (30 ml), 1% aq. HCl solution (30 ml) and water (30 ml) and the resultant organic layer was distilled completely u/v and co-distilled with ethanol to obtain crude. The obtained crude was dissolved in ethanol (270 ml) at reflux temperature and then distilled the resultant reaction mass upto ~20 vol at 40° C. Reaction mass was cooled to 25-35° C. then filtered the solid and washed with ethanol (6 ml). The resulting wet cake was dried under vacuum at 60-65° C. to obtain title compound. Yield: 4.0 g.

Example—3: Preparation of Ivacaftor

N-(2,4-di-tert-butyl-5-hydroxyphenyl)-1-benzyl-4-oxo-1,4-dihydroquinoline-3-carboxamide (3 g; obtained from Ex-2) and dimethylformamide (45 ml), 20% palladium hydroxide (3 g) and ammonium formate (3 g) were charged into a round bottom flask at 25-30° C. The reaction mass was heated to 70-80° C. and stirred for 3 hours. Then the reaction mass was cooled to 40° C. and filtered. To the filtered mass water (180 ml) was added at 5-10° C., then the reaction mass was stirred for 30 min at 25-30° C. and filtered the precipitated solid and solid bed washed with water (15 ml). The obtained wet cake was dissolved in ethyl acetate (90 ml) and filtered through celite bed and bed washed with ethyl acetate (10 ml). Filtrate was distilled completely u/v at below 50° C. and crude product co-distilled with ethanol (10 ml), charged ethanol (15 ml) to crude product and stir for 30 min at 25-35° C. Filtered the obtained solids and washed with ethanol (6 ml). Dry the material at 60-65° C. for 18 to 24 hrs to obtain Ivacaftor. Yield: 2.0 g.

Example—4: Preparation of Compound of Formula XIa 2-fluorobenzoic acid (30 g), Meldrum acid (27.7 g), 4-dimethylaminopyridine (39.2 g) and methylene chloride (300 ml) were charged into a round bottom flask at 25-35° C. To the reaction mass was added pre dissolved solution of dicyclohexylcarbodiimide (57.6 g) in methylene chloride (150 ml) over a period of 1 hr at 25-35° C. stirred at for 2-3 hr at same temperature. After completion of the reaction, charged 10% aq HCl (300 ml) and stirred for 15-20 min, separated the obtained salts from reaction mass by filtration and the resultant filterate was washed with 10% HCl (150 ml) and water (150 ml). Organic layer was distilled completely under vacuum at below 40° C. and co-distilled with diisopropylether (60 ml). The resultant reaction mass was treated with diisopropylether (150 ml) and stirred for 30 min. Filtered the obtained solids and washed with diisopropylether (60 ml). Dry the material at 40-55° C. to obtain title compound. Yield: 45.0 g; $^1$H NMR (CDCl$_3$): δ7.62 (d, 2H), δ7.3 (m, 1H), δ7.1 (m, 1H), δ5.2 (s, 1H), δ1.9 (s, 6H); ESI MS: 265 m/z (MH$^-$).

Example—5: Preparation of Compound of Formula VIa 5-amino-2,4-di-tert-butyl phenol hydrochloride (7.7 g), diisopropylethylamine (3.9 g) and toluene (200 ml) were charged into a round bottom flask at 25-35° C. Reactions mass was heated to 95-105° C. and was charged compound of Formula XIa (10 g) in lot wise and stirred for 2-3 hr at reflux temperature. After completion of the reaction, reaction mass was distilled completely under vacuum at below 50° C. and co-distilled with heptane. The resultant reaction mass was stirred with heptane (50 ml) for 30 min. Filtered the obtained solids and dryed the material to obtain title compound. Yield: 12.0 g; $^1$H NMR (CDCl$_3$): δ9.2 (s, 1H), δ7.9 (m, 2H), δ7.54 (s, 1H), δ7.3 (m, 2H), δ7.1 (s, 1H), δ4.2 (s, 2H), δ1.37 (s, 9H), δ1.34 (s, 9H); ESI MS: 384 m/z (MH$^-$).

Example—6: Preparation of Compound of Formula VIIa

Compound of Formula VIa (1 g) and toluene (10 ml) were charged into a round bottom flask at 25-35° C. Reactions mass was heated to 60-65° C. and was charged dimethylformamide dimethyl acetal (1.2 g) and stirred for overnight at same temperature. After completion of the reaction, distilled the reaction mass was completely under vacuum at below 50° C. to obtain crude compound. The obtained crude was purified by column chromatography to obtain title compound. Yield: 1.0 g; $^1$H NMR (CDCl$_3$): δ9.2 (s, 1H), δ7.9 (m, 2H), δ7.54 (s, 1H), δ7.3 (m, 2H), δ7.1 (s, 1H), δ3.9 (s, 1H), δ3.2 (s, 6H), δ1.37 (s, 9H), δ1.34 (s, 9H); ESI MS: 441 m/z (MH$^+$).

Example—7: Preparation of Compound of Formula XIIa

Compound of Formula XIa (10 g) and ethanol (50 ml) were charged into a round bottom flask at 25-35° C. Reaction mass was heated to reflux and stirred for 2-3 hr at and temperature. After completion of the reaction, reaction mass was distilled completely under vacuum at below 50° C. and co-distilled with heptane. The resultant reaction mass was stirred with heptane (25 ml) for 30 min. Filtered the obtained solids and dryed the material to obtain title compound. Yield: 7.0 g; $^1$H NMR (CDCl$_3$): δ8.0 (m, 1H), δ7.6 (m, 1H), δ7.2 (m, 1H), δ7.1 (m, 1H), δ3.7 (m, 2H), δ3.6 (s, 2H), δ1.1 (s, 3H); ESI MS: 211 m/z (MH$^+$).

Example—8: Preparation of Compound of Formula VIa 5-amino-2,4-di-tert-butyl phenol hydrochloride (5.3 g), diisopropylethylamine (2.7 g) and toluene (100 ml) were charged into a round bottom flask at 25-35° C. Reactions mass was heated to 95-105° C. and was charged compound of Formula XIIa (5 g) in lot wise and stirred for 2-3 hr at reflux temperature. After completion of the reaction, reaction mass was distilled completely under vacuum at below 50° C. and co-distilled with heptane. The resultant reaction mass was stirred with heptane (25 ml) for 30 min. Filtered the obtained solids and dryed the material to obtain title compound. Yield: 7.0 g.

Example—9: Preparation of Ivacaftor

Compound of Formula VIIa (1 g; obtained from Ex-5), ethanol (10 ml) and ammonium hydroxide (5 ml) were charged into a round bottom flask at 25-35° C. and stirred for 1 hr at same temperature. After completion of the reaction, reaction mass was distilled completely under vacuum at below 50° C. and co-distilled with ethanol (10 ml) to obtain residue. The obtained residue was dissolved in dimethylformamide (5 ml) and charged potassium carbonate (0.67 g) at 25-30° C. Reactions mass was heated to 85-95° C. and stirred for 2 hr at same temperature. After completion of the reaction, cooled the reaction mass to 25-30° C. and slowly added water (25 ml) over a period of 1 hr and stirred for 1 hr at same temperature. Filtered the obtained solids and washed with water (2×10 ml) and dryed under vacuum. The obtained solids were dissolved in ethyl acetate (10 ml) and washed with water (5 ml). Organic layer was distilled completely under vacuum and co-distilled with ethanol (10 ml) to obtain residue. The obtained residue was added ethanol (5 ml) at room temperature and the reaction mass was heated to 75-80° C. and stirred for 1 hr. Reaction mass was cooled to 25-35° C. and filtered the solids obtained and washed with ethanol (2 ml). Dry the material at 45-50° C. to obtain title compound. Yield: 0.55 g.

Example—10: Preparation of Compound of Formula VIIb

Compound of Formula VIIb was prepared from compound of formula VIb analogously process according to Example—6.

Example—11: Preparation of Ivacaftor

Compound VIIb (1.0 g), iron powder (0.48 g) and ethanol (10.0 ml) were charged into a round bottom flask at 25-35° C. and heated to 65° to 75° C. To the reaction mass was added ammonium chloride solution (1.14 g dissolved in water 5 ml) at 65 to 75° C. for 60 to 90 min and stirred for 2 to 3 hr at same temperature. After the completion of the reaction, reaction mass was cooled to 25-35° C. and distilled reaction mass under vacuum at 50° C. to obtain a residue. To the obtained residue was added ethylacetate (10.0 ml) and water (10 ml) and stirred for 10 min and separated the organic layer, washed the organic layer with water (10 ml) and distilled the reaction mass at 45 to 50° C. and co-distilled with ethanol (10 ml) to obtain a residue. The obtained residue was added ethanol (5 ml) at room temperature and the reaction mass was heated to 75-80° C. and stirred for 1 hr. Reaction mass was cooled to 25-35° C. and filtered the solids obtained and washed with ethanol (2 ml). Dry the material at 45-50° C. to obtain title compound. Yield: 0.7 g.

Example—11: Preparation of Compound of Formula XIIa 2-fluorobenzoic acid (10 g) toluene (80 ml) and dimethyl formamide (0.1 ml) were charged into a round bottom flask at 25-35° C. To the reaction mass thionyl chloride (12.7 g) was added slowly over a period of 30 min at same temperature. Reaction mass was heated to reflux and stirred for 3-4 hr. After completion of the reaction, reaction mass was cooled to 55-65° C. and distilled completely under vacuum at 55-65° C. and co-distilled with toluene (2×20 ml) to obtain residue and the residue was dissolved in tetrahydrofuran (50 ml). Tetrahydrofuran (150 ml) and magnesium chloride (24.5 g) was added in another round bottom flask at 25-35° C. Reaction mass was cooled to 10-15° C. and was added potassium salt of monoethylmalonate (36.4 g) at same temperature. To the reaction mass was added triethyl amine (21.6 g) slowly over a period of 30 min and reaction mass was heated to 25-35° C. and stirred for 8 hr at same temperature. To the reaction mass was added above pre dissolved tetrahydrofuran solution of 2-fluorobenzoyl chloride at 15-25° C. and stirred for 16 hr at 25-35° C. After completion of the reaction, reaction mass was distilled completely under vacuum at below 50° C. and cooled to 25-35° C. To the resultant reaction mass was added water (400 ml) and stirred for 3 hr at same temperature. Filtered the precipitated solids and washed with water (10 ml). The obtained solids were stirred with water (200 ml), and a mixture of water (100 ml) and sodium bicarbonate (50 g), a mixture of water (100 ml) and hydrochloric acid (10 ml) sequentially at 25-35° C. and filtered the solid and washed with water (10 ml). The obtained solid was stirred with methanol (20 ml) for 40 min at 25-35° C. Filtered the solids and washed with methanol (10 ml) and dryed the material to obtain title compound. Yield: 13.5 g.

Example—12: Preparation of Compound of Formula VIp'

5-Amino-2,4-di-tert-butylphenylmethyl carbonate (5 g), compound of Formula XIa (6.19 g; obtained from Ex-4) and ethyl acetate (50 mL) were charged in to round bottom flask at 25-35° C. and stirred for 2 hrs at same temperature. Reaction mass was heated to 40° C. and stirred for 2 hrs at same temperature and was further heated to 60° C. and stirred for 2 hrs. After completion of reaction, reaction mass was distilled out completely under vacuum at 50° C. and co-distilled with n-Heptane (2×20.0 mL). To the resultant reaction mass was charged n-heptane (30 mL) at 25-35° C. and stirred for 60 min. filtered the obtained solids and dried the material at 40-45° C. to get title compound of 2,4-di-tert-butyl-5-(3-(2-fluorophenyl)-3-oxopropanamido) phenyl methyl carbonate of Formula VIp. Yield: 7.9 g; $^1$H NMR (CDCl$_3$): δ9.2 (brs, 1H), δ7.9 (d, 2H), δ7.65 (t, 1H), δ7.5 (s, 1H), δ7.4 (s, 1H), δ7.2 (t, 1H), δ4.2 (s, 2H), δ3.90 (S, 3H), δ1.37 (s, 9H), δ1.34 (s, 9H); ESI MS 442 m/z (M$^-$H).

Example—13: Preparation of Compound of Formula XIIIp

Compound of Formula VIp' (6 g; obtained from Ex-12), acetic anhydride (8.95 mL), triethylorthoformate (15.75 mL) and zinc chloride (0.16 g) were charged in to round bottom flask at 25-35° C. and stirred for 6 hrs at same temperature. After completion of reaction, reaction mass was quenched with water (30 mL) and compound was extracted with ethyl 40 acetate (60 mL). Resultant organic layer was washed with water (30 mL) and distilled completely under vacuum at below 50° C. to get title compound of Formula XIIIp. Yield: 6.75 g; $^1$HNMR (300 MHz, CDCl$_3$): δ10.23 (brs, 1H), δ9.3 (d, 1H), δ8.5 (s, 1H), δ7.69 (t, 1H), δ7.56 (t, J=7.5 Hz, 1H), δ7.48 (d, 1H), δ7.38 (s, 1H), δ7.25 (s, 1H), δ3.89 (s, 3H), δ2.30 (s, 2H), δ1.37 (s, 9H), δ1.33 (s, 9H); ESI MS–500 m/z (M+1).

Example—14: Preparation of Ivacaftor

Compound of Formula XIIIp (6.75 g), ethanol (70 mL) and ammonium hydroxide (35 mL) were charged in to round bottom flask at 25-35° C. Reaction mass was heated to reflux and stirred for 10 to 12 hrs at same temperature. After completion of reaction, reaction mass was distilled at 45-50° C. under vacuum and co-distilled with ethanol (10 mL) to obtain a residue. The obtained residue was dissolved in dimethylformamide (54 mL) and charged potassium carbonate (5.94 g) at 25-30° C. Reactions mass was heated to 100-105° C. and stirred for 12 hrs at same temperature. After completion of the reaction, cooled the reaction mass to 25-30° C. and slowly added water (270 mL) and pH of the reaction mass was adjusted to 2.0 with aq hydrochloric acid. Filtered the precipitated solids and was charged ethanol (200 mL) and heated to 75-80° C. and stirred for a period of 60 min at same temperature. Reaction mass was cooled to 25-35° C. and distilled reaction mass to 60 mL. Filtered the solids obtained and washed with ethanol (12 ml). Dry the material at 45-50° C. to obtain title compound. Yield: 5.0 g.

Example—15: Preparation of (E)-3-Ethoxyacryloyl Chloride of Formula XVIa

To a 250 ml round bottom flask ethyl vinyl ether (25 g) was added drop wise to oxalyl chloride (66 g) at 0° C. The mixture was allowed to warm to room temperature and stirred for 12 hrs at same temperature. After completion of the reaction, oxalyl chloride was distilled off and the residue heated to 120° C. for 30 min. Then the resultant crude residue was purified by vacuum distillation to yield (E)-3-ethoxyacryloyl chloride of Formula XVIa. Yield: 23.8 g; $^1$H-NMR (CDCl$_3$): δ7.78 (1H, d), 65.51 (1H, d), 64.05 (2H, q), 61.40 (3H, t); B.P: 85-87° C.

Example—16: Preparation of Compound of Formula IVp 2,4-di-tert-butyl-5-nitro phenol (30 g), N,N-dimethyl-amino pyridine (0.73 g), triethylamine (24.16 g) and methylene chloride (120 mL) were charged in to round bottom flask at 25-35° C. Reaction mass was cooled to 0-5° C., methyl chloro formate (16.92 g) was slowly added over a period of 60 min and reaction mass was heated to 25-30° C. After completion of the reaction, filtered the reaction mass and washed with ethyl acetate (150 mL). Combined organic layer distilled completely under vacuum at below 40° C. Then the resultant crude mass was dissolved in to ethyl acetate (3000 mL) and washed with water (150 mL) and 5% aqueous hydrochloride solution (150 mL) and followed by water (150 mL). Organic layer was distilled completely to get 2,4-di tert-butyl-5-nitro phenyl methyl carbonate (36.6 g). To the obtained 2,4-di-tert-butyl-5-nitro phenyl methyl carbonate (22.5 g) was added aqueous ammonium chloride (38.90 g), ethanol (225), Iron (16.23 g) at room temperature and heated to reflux for 3 hrs. After completion of the reaction, temperature was cooled to 30° C. and filtered through celite. The celite was washed with ethanol and combined filtrates were distilled completely under vacuum at below 50° C. To the obtained reaction mass water (112 mL) was added at 25-35° C. and stirred for 30 min and filtered the precipitated solid and washed with water (60 mL) to get 5-amino-2,4-di-tert-butyl phenyl methyl carbonate of Formula IVp as a white solid (18.75 g).

Example—17: Preparation of Compound of Formula XVIIa

5-Amino 2,4-di-tert-butyl phenyl methyl carbonate (7 g), methylene chloride (70 mL), pyridine (4.95 g) were charged in to round bottom flask at 25-35° C. and stirred for 15 min at same temperature. Reaction mass was cooled to 0-5° C., methylene chloride (35 mL) solution of (E)-3-ethoxyacryloyl chloride of Formula XVIa (3.71 g) was added slowly over a period of 20-30 min. Reaction mass temperature was raised to 25-35° C. and stirred for 5 hrs. After completion of the reaction, reaction mass was washed with water (70 mL), 5% sodium bicarbonate (70 mL) and followed by water (70 mL) sequentially. Organic layer was distilled completely under vacuum and the resultant crude product was purified by column purification using ethyl acetate/hexane to get title compound as a cream coloured solid. Yield: 8 g; $^1$H-NMR (CDCl$_3$); δ7.6 (d, 1H) δ7.46 (s, 1H), δ7.26 (s, 1H), δ6.83

(brd, 1H), δ3.96 (q, 2H), δ3.89 (s, 3H), δ 1.4 (d, 3H), δ1.25 (s, 9H), δ1.24 (s, 9H); ESI MS: 378 m/z (MH⁺).

Example—18: Preparation of Compound of Formula XIIIa

[(E)-3-ethoxyprop-2-enoyl]-5-amino-2,4-di-tert-butyl phenyl methyl carbonate of Formula XVIIa (0.5 g), triethylamine (0.4 mL) and toluene (5 mL) were charged in to round bottom flask at 25-35° C. Reaction mass was heated to 50-55° C. and slowly added 2-fluoro benzoyl chloride (0.35 g in toluene 2.5 mL) over a period of 10 min and stirred for 5 hrs at same temperature. After completion of the reaction, reaction mass was cooled to 25-35° C. and washed with water and followed by sodium bicarbonate. Organic layer was distilled completely under vacuum at below 50° C. and co-distilled with heptane. To the resultant reaction mass heptane (5 mL) was added and stir for 30 min. Filtered the obtained solid to get 2,4-di-tert-butyl-5-(3-ethoxy)-2-(2-fluorobenzoyl)acrylamido)phenyl methyl carbonate of Formula XIIIa as a cream color solid. Yield: 0.66 g; ¹H-NMR (CDCl₃): δ10.23 (brs, 1H), δ9.3 (d, 1H), δ8.5 (s, 1H), δ7.69 (t, 1H), δ7.56 (t, 1H), δ7.48 (d, 1H), δ7.38 (s, 1H), δ7.25 (s, 1H), δ3.89 (s, 3H), δ2.30 (s, 2H), δ1.37 (s, 9H), δ1.33 (s, 9H); Mass (M+1)–500.

It will be understood that various modifications may be made to the embodiments disclosed herein. Therefore the above description should not be constructed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. A process for the preparation of ivacaftor of Formula I or a pharmaceutically acceptable salt thereof, Formula I comprising:
a) reacting a compound of Formula XII with a compound of Formula IVa or a salt thereof in the presence of a base in a solvent to obtain a compound of Formula VI, Formula XII Formula IVa Formula VI and
b) converting the compound of Formula VI into the ivacaftor of Formula I,
wherein when 'X' is a halo, then 'R1' represents either hydrogen or a protecting group, and when 'X' is nitro, then 'R1' is hydrogen, and wherein 'Z' represents one of a $C_1$-$C_5$ alkoxy and a halogen.

2. The process of claim 1, wherein the protecting group is selected from the group consisting of methoxycarbonyl, methoxymethyl, benzyloxymethyl, tetrahydropyranyl, benzyl, benzoyl, p-methoxybenzyl, p-nitrobenzyl, o-nitrobenzyl, p-nitrobenzoyl and trimethylsilyl, wherein the halo is one of fluoro, chloro, bromo and iodo, and wherein the $C_1$-$C_5$ alkoxy is one of methoxy, ethoxy, isopropoxy, butyloxy, and pentyloxy.

3. The process of claim 1, wherein, when the compound of Formula VI is the compound of Formula VIb, the step b) comprises:
a2) reacting a compound of Formula VIb with a dimethyl formamide-dimethyl amine complex to obtain a compound of Formula VIIb, Formula VIb -continued

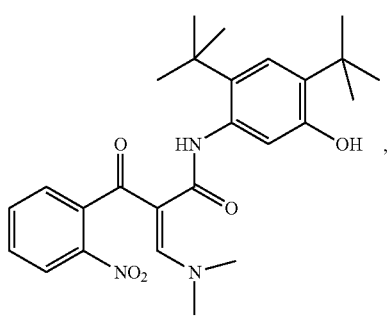

Formula VIIb b2) reducing the compound of Formula VIIb in presence of a reducing agent to obtain a compound of Formula X,

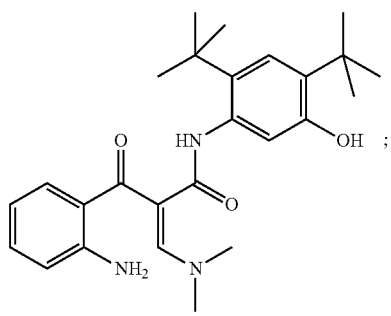

Formula X and c2) converting the compound of Formula X into the ivacaftor of Formula I.

4. The process of claim 3, wherein the step a2) is carried out in presence of an organic solvent selected from the group consisting of acetonitrile, propionitrile, tetrahydrofuran, dimethyl ether, methyl tertiary butyl ether, dimethoxyethane, toluene, xylene, and mixtures thereof.

5. The process of claim 3, wherein the reducing agent is selected from the group consisting of Fe/ammonium chloride, Fe/ammonium formate, Fe/HCl, hydrogen gas, palladium on carbon, raney nickel, platinum oxide, sodium hydrosulfite, and zinc.

6. The process of claim 3, wherein the reduction step b2) is carried out in presence of a solvent selected from the group consisting of tetrahydrofuran, 2-methyltetrahydrofuran, dimethyl ether, methyl tertiary butyl ether, methanol, ethanol, isopropanol, dimethylformamide, dimethylsulfoxide, dimethyl acetamide, N-methyl pyrrolidinone, water, and mixtures thereof.

7. The process of claim 1, wherein the compound of Formula XII is the compound of Formula XI, wherein when 'X' is a halo, then 'R1' is either hydrogen or a protecting group, and when 'X' is nitro, then '$R_1$' is hydrogen.

8. The process of claim 7, wherein 'R1' represents one of hydrogen and methoxycarbonyl.

9. The process of claim 7, wherein the halo represents one of fluoro, chloro, bromo, and iodo.

10. The process of claim 1, wherein the $R_1$ is hydrogen, wherein the halo group is chloro, and wherein the $C_1$-$C_5$ alkoxy group is an ethoxy group.

11. The process of claim 1, wherein the base is selected from the group consisting of sodium hydroxide, potassium hydroxide, sodium methoxide, sodium ethoxide, sodium tert-butoxide, potassium tert-butoxide, sodium carbonate, potassium carbonate, cesium carbonate, sodium bicarbonate, potassium bicarbonate, triethylamine, isopropylethylamine, diisopropylamine, diisopropylethylamine, N-methylmorpholine, piperidine, pyridine, and mixtures thereof.

12. The process of claim 1, wherein the solvent is selected from the group consisting of dimethyl formamide, dimethyl acetamide, N-methyl pyrrolidinone, methylene chloride, ethylene chloride, toluene, xylene, and mixtures thereof.

13. The process of claim 1, wherein the solvent is toluene, and wherein the base is diisopropylethylamine.

14. The process of claim 1, further comprising:
a5) reacting the compound of Formula VI with ($C_{1-5}$ alkyl)$_3$-orthoformate in presence of a Lewis acid in a solvent to obtain a compound of Formula XIII,

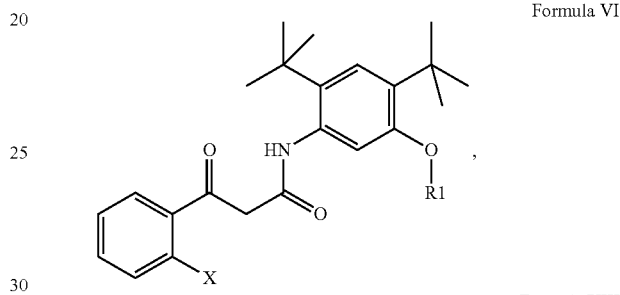

Formula VI

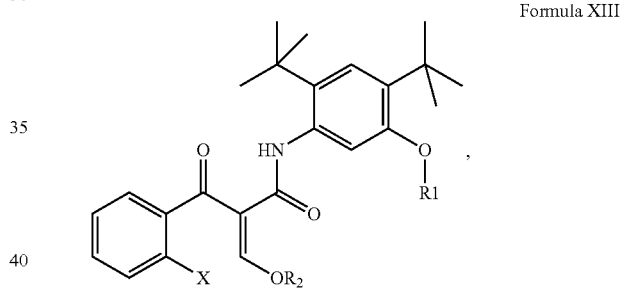

Formula XIII wherein 'X' represents a halo or $NO_2$, wherein 'R1' represents either hydrogen or a protecting group, and wherein 'R2' represents a $C_{1-5}$ alkyl;

b5) reacting the compound of Formula XIII with a source of ammonia in a solvent to obtain a compound of Formula VIII,

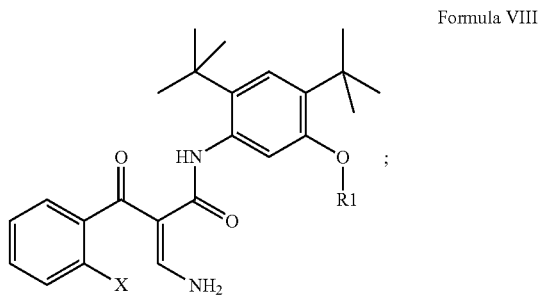

Formula VIII and c5) cyclizing the compound of Formula VIII in presence of a base to obtain the ivacaftor of Formula I, when 'R1' is hydrogen, or to obtain a compound of Formula IX, when 'R1' is a protecting group, and deprotecting the Formula IX in presence of a deprotecting agent to obtain the ivacaftor of Formula I,

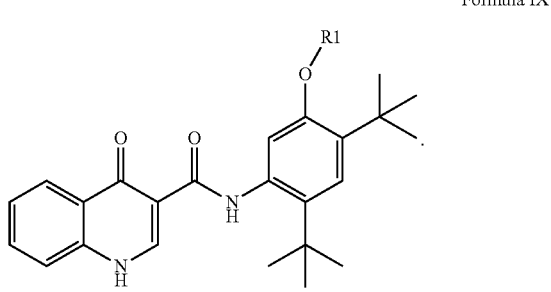

Formula IX

15. The process of claim 14, wherein the protecting group is selected from the group consisting of methoxycarbonyl, methoxymethyl, benzyloxymethyl, tetrahydropyranyl, benzyl, benzoyl, p-methoxybenzyl, p-nitrobenzyl, o-nitrobenzyl, p-nitrobenzoyl and trimethylsilyl, wherein the halo is one of fluoro, chloro, bromo, and iodo, and wherein the $C_{1-5}$ alkyl is one of methyl, ethyl, propyl, butyl, and pentyl.

16. The process of claim 14, wherein the protecting group is methoxycarbonyl, wherein the halo group is chloro, and wherein the $C_{1-5}$ alkyl group is ethyl.

17. The process of claim 14, wherein the 'R1' is hydrogen, wherein the halo group is chloro, and wherein the $C_{1-5}$ alkyl group is ethyl.

18. The process of claim 14, wherein the $(C_{1-5}$ alkyl$)_3$-orthoformate is selected from the group consisting of trimethyl orthoformate, triethyl orthoformate, tripropyl orthoformate, tributyl orthoformate, and tripentyl orthoformate.

19. The process of claim 14, wherein the Lewis acid is selected from the group consisting of zinc chloride, tin(IV) chloride, tin(II) chloride, aluminium chloride, and boron trifluoride.

20. The process of claim 14, wherein the solvent of step a5) is selected from the group consisting of acetic anhydride, propionic anhydride acetonitrile, propionitrile, tetrahydrofuran, dimethyl ether, methyl tertiary butyl ether, dimethoxyethane, toluene, xylene, and mixtures thereof.

21. The process of claim 14, wherein the $(C_{1-5}$ alkyl$)_3$-orthoformate is triethyl orthoformate, wherein the Lewis acid is zinc chloride, and wherein the solvent is acetic anhydride.

22. The process of claim 14, wherein the source of ammonia is selected from the group consisting of ammonia gas, ammonium hydroxide, ammonium acetate, and ammonium formate.

23. The process of claim 14, wherein the solvent of step b5) is selected from the group consisting of methanol, ethanol, isopropanol, dimethyl formamide, dimethyl acetamide, N-methyl pyrrolidinone, toluene, xylene, water, and mixtures thereof.

24. The process of claim 14, wherein the source of ammonia is ammonium hydroxide, and wherein the solvent is ethanol.

25. The process of claim 14, wherein the base of step c5) is selected from the group consisting of sodium hydroxide, potassium hydroxide, sodium methoxide, sodium ethoxide, sodium tert-butoxide, potassium tert-butoxide, sodium carbonate, potassium carbonate, cesium carbonate, sodium bicarbonate, potassium bicarbonate, triethylamine, isopropylethylamine, diisopropylamine, diisopropylethylamine, N-methylmorpholine, piperidine, pyridine, and mixtures thereof.

26. The process of claim 14, wherein the step c5) of cyclization is carried out in presence of a solvent selected from the group consisting of tetrahydrofuran, 2-methyl tetrahydrofuran, dimethyl ether, methyl tertiary butyl ether, methanol, ethanol, isopropanol, toluene, xylene, dimethylformamide, dimethyl acetamide, N-methyl pyrrolidinone, dimethylsulfoxide, sulfolane, acetonitrile, propionitrile, and mixtures thereof.

27. The process of claim 14, wherein the deprotecting agent is selected from the group consisting of hydrochloric acid, hydrobromic acid, trifluoro acetic acid, potassium carbonate, sodium hydroxide, sodium ethoxide, and mixture thereof.

28. The process of claim 14, wherein the deprotection is carried out in presence of a solvent selected from the group consisting of methanol, ethanol, isopropanol, acetone, methyl isobutyl ketone, methyl ethyl ketone, tetrahydrofuran, 2-methyl tetrahydrofuran, methyl tertiary butyl ether, dimethyl formamide, dimethylsulfoxide, dimethyl acetamide, N-methyl pyrrolidinone, and mixtures thereof.

29. The process of claim 14, wherein, when the compound of Formula VI is a compound of Formula VIb and the compound of Formula XIII is a compound of Formula XIV, wherein 'R2' represents $C_{1-5}$ alkyl, a6) reacting the compound of Formula VIb with $(C_{1-5}$ alkyl$)_3$-orthoformate in presence of a Lewis acid to obtain the compound of Formula XIV,

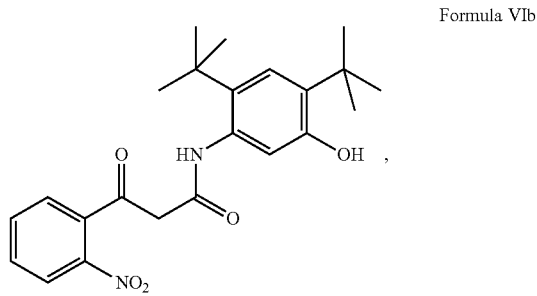 [SMILES: CC(C)(C)c1cc(C(C)(C)C)c(NC(=O)CC(=O)c2ccccc2[N+](=O)[O-])cc1O]

Formula VIb

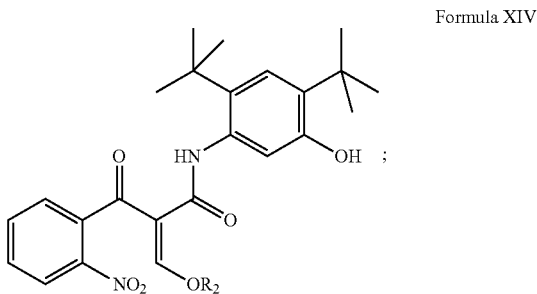

Formula XIV b6) reducing the compound of Formula XIV in presence of a reducing agent to obtain a compound of Formula XV,

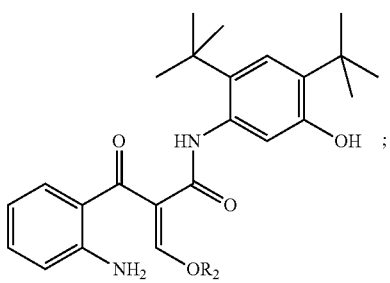

Formula XV and
c6) cyclizing the compound of Formula XV in presence of a base into the ivacaftor.

30. The process of claim 29, wherein the $C_{1-5}$ alkyl represents one of methyl, ethyl, propyl, butyl, and pentyl.

31. The process of claim 29, wherein the $(C_{1-5}$ alkyl$)_3$-orthoformate is selected from the group consisting of trimethyl orthoformate, triethyl orthoformate, tripropyl orthoformate, tributyl orthoformate, and tripentyl orthoformate.

32. The process of claim 29, wherein the Lewis acid is selected from the group consisting of zinc chloride, tin(IV) chloride, tin(II) chloride, aluminium chloride, and boron trifluoride.

33. The process of claim 29, wherein the $(C_{1-5}$ alkyl$)_3$-orthoformate is triethyl orthoformate and wherein the Lewis acid is zinc chloride.

34. The process of claim 29, wherein the step a6) is carried out in presence of a solvent selected from the group consisting of acetic anhydride, propionic anhydride acetonitrile, propionitrile, tetrahydrofuran, dimethyl ether, methyl tertiary butyl ether, dimethoxyethane, toluene, xylene, and mixtures thereof.

35. The process of claim 29, wherein the reducing agent is selected from the group consisting of Fe/ammonium chloride, Fe/ammonium formate, Fe/HCl, hydrogen gas, palladium on carbon, raney nickel, platinum oxide, sodium hydrosulfite, and zinc.

36. The process of claim 29, wherein the reducing agent is Fe/ammonium chloride.

37. The process of claim 29, wherein the reduction step b6) is carried out in presence of a solvent selected from the group consisting of tetrahydrofuran, 2-methyltetrahydrofuran, dimethyl ether, methyl tertiary butyl ether, methanol, ethanol, isopropanol, dimethylformamide, dimethylsulfoxide, dimethyl acetamide, N-methyl pyrrolidinone, water, and mixtures thereof.

38. The process of claim 29, wherein the base of step c6) is selected from the group consisting of sodium hydroxide, potassium hydroxide, sodium methoxide, sodium ethoxide, sodium tert-butoxide, potassium tert-butoxide, sodium carbonate, potassium carbonate, cesium carbonate, sodium bicarbonate, potassium bicarbonate, triethylamine, isopropylethylamine, diisopropylamine, diisopropylethylamine, N-methylmorpholine, piperidine, pyridine and mixtures thereof.

39. The process of claim 29, wherein the step c6) of cyclization is carried out in presence of a solvent, wherein the solvent is selected from the group consisting of tetrahydrofuran, 2-methyl tetrahydrofuran, dimethyl ether, methyl tertiary butyl ether, methanol, ethanol, isopropanol, toluene, xylene, dimethylformamide, dimethyl acetamide, N-methyl pyrrolidinone, dimethylsulfoxide, sulfolane, acetonitrile, propionitrile, and mixtures thereof.

40. A compound selected from the group consisting of Formula VI or a pharmaceutically acceptable salt thereof,

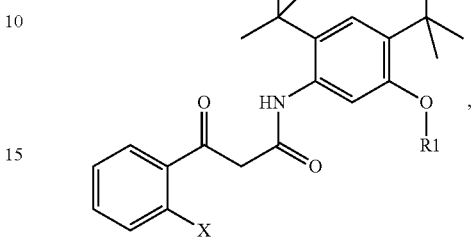

Formula VI wherein 'X' represents a chloro, and wherein 'R1' represents either hydrogen or a protecting group;
a compound of Formula VIII or a pharmaceutically acceptable salt thereof,

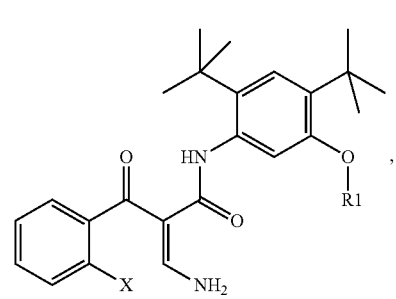

Formula VIII wherein 'X' represents a halo, and wherein 'R1' represents either hydrogen or a protecting group; and
a compound of Formula XV or a pharmaceutically acceptable salt thereof,

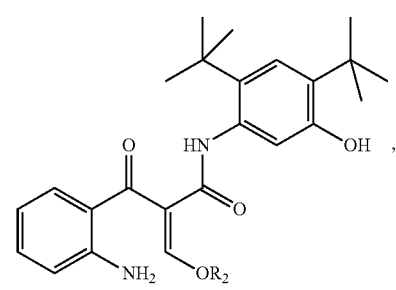

Formula XV wherein 'R2' represents a $C_{1-5}$ alkyl.

41. The process of claim 1, further comprising:
preparing a pharmaceutical composition by combining the ivacaftor of Formula I or the pharmaceutically acceptable salt thereof with at least one pharmaceutically acceptable excipient.

* * * * *